US012569344B2

(12) United States Patent
Abbott et al.

(10) Patent No.: US 12,569,344 B2
(45) Date of Patent: Mar. 10, 2026

(54) DEVICES, SYSTEMS, AND METHODS FOR CLAMPING A LEAFLET OF A HEART VALVE

(71) Applicant: Boston Scientific Scimed, Inc., Maple Grove, MN (US)

(72) Inventors: Aaron Abbott, Columbia Heights, MN (US); Joseph Walker, Shoreview, MN (US); Joel T. Eggert, Plymouth, MN (US); Daniel Shuey, Pine City, MN (US); Christopher J. Koudela, New London, MN (US); Troy A. Giese, Blaine, MN (US); Larry M. Killeen, Elk River, MN (US); James P. Rohl, Prescott, WI (US); Mitchell Nelson, Hudson, WI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 768 days.

(21) Appl. No.: 17/899,576

(22) Filed: Aug. 30, 2022

(65) Prior Publication Data

US 2023/0123832 A1 Apr. 20, 2023

Related U.S. Application Data

(60) Provisional application No. 63/239,467, filed on Sep. 1, 2021.

(51) Int. Cl.
*A61F 2/24* (2006.01)

(52) U.S. Cl.
CPC .......... *A61F 2/2466* (2013.01); *A61F 2/2457* (2013.01); *A61F 2220/0016* (2013.01); *A61F 2220/0033* (2013.01)

(58) Field of Classification Search
CPC .... A61F 2/2466; A61F 2/2454; A61F 2/2457; A61F 2/246; A61F 2/2463; A61B 2017/0488; A61B 17/128; A61B 17/122
See application file for complete search history.

(56) References Cited

U.S. PATENT DOCUMENTS

| | | | |
|---|---|---|---|
| 5,156,609 A | 10/1992 | Nakao et al. | |
| 5,725,542 A | 3/1998 | Yoon | |
| | (Continued) | | |

FOREIGN PATENT DOCUMENTS

| CN | 118453200 A | * | 8/2024 | ............... A61F 2/24 |
|---|---|---|---|---|
| WO | WO-2023064353 A2 | * | 4/2023 | ......... A61B 17/0487 |
| WO | WO-2025085321 A1 | * | 4/2025 | ............. A61F 2/246 |

OTHER PUBLICATIONS

International Search Report and Written Opinion dated Jan. 30, 2023 for International Application No. PCT/US2022/042096.

*Primary Examiner* — Alvin J Stewart
(74) *Attorney, Agent, or Firm* — Seager, Tufte & Wickhem, LLP

(57) ABSTRACT

A clip and a clip deployment and delivery system. The clip may be engaged with a clip spreader such that simple relative movement, such as sliding movement, between the clip and clip spreader causes the clip and clip spreader to disengage from each other. A clip spreader actuator may be coupled to one arm of the clip spreader, extend distally around a distal end of the clip spreader, proximally along the other clip spreader arm, and to a proximal end at which the actuator may be controlled to open or close the clip spreader. The clips may be leaflet clips having teeth on one arm thereof and bumps on another arm thereof. The arms of the leaflet clip may be biased into a closed configuration by a flex zone which has an expanded portion extending laterally away from only one of the clip arms.

14 Claims, 10 Drawing Sheets

(56) References Cited

U.S. PATENT DOCUMENTS

| | | | | |
|---|---|---|---|---|
| 7,569,062 | B1* | 8/2009 | Kuehn | A61B 17/0643 |
| | | | | 623/2.11 |
| 7,736,388 | B2 | 6/2010 | Goldfarb et al. | |
| 7,942,885 | B2* | 5/2011 | Sixto, Jr. | A61B 17/1285 |
| | | | | 606/143 |
| 8,252,050 | B2 | 8/2012 | Maisano et al. | |
| 9,220,507 | B1* | 12/2015 | Patel | A61B 17/064 |
| 9,681,864 | B1 | 6/2017 | Gammie et al. | |
| 10,111,751 | B1* | 10/2018 | Metchik | A61F 2/2463 |
| 10,136,993 | B1 | 11/2018 | Metchik et al. | |
| 10,188,392 | B2* | 1/2019 | Wei | A61B 17/08 |
| 10,667,804 | B2 | 6/2020 | Basude et al. | |
| 10,667,815 | B2 | 6/2020 | Krone et al. | |
| 10,779,829 | B2* | 9/2020 | Wei | A61F 2/246 |
| 10,799,356 | B2 | 10/2020 | McAfee et al. | |
| 11,185,413 | B2* | 11/2021 | Basude | A61F 2/2463 |
| 11,224,511 | B2* | 1/2022 | Dixon | A61F 2/246 |
| 11,883,290 | B2* | 1/2024 | Basude | A61F 2/246 |
| 11,992,222 | B2* | 5/2024 | Shellenberger | A61B 17/122 |
| 12,023,041 | B2* | 7/2024 | Shellenberger | A61B 17/1285 |
| 12,114,866 | B2* | 10/2024 | Thomas | A61B 17/128 |
| 12,208,008 | B2* | 1/2025 | Eggert | A61B 17/1227 |
| 12,279,774 | B2* | 4/2025 | Castro | A61B 17/10 |
| 12,290,439 | B2* | 5/2025 | Padala | A61F 2/2463 |
| 12,295,846 | B2* | 5/2025 | Abunassar | A61B 17/00234 |
| 2005/0090838 | A1* | 4/2005 | Sixto | G01B 7/10 |
| | | | | 606/139 |
| 2008/0234703 | A1 | 9/2008 | Cropper et al. | |
| 2009/0105729 | A1 | 4/2009 | Zentgraf | |
| 2010/0161042 | A1 | 6/2010 | Maisano et al. | |
| 2015/0250590 | A1 | 9/2015 | Gries et al. | |
| 2015/0374493 | A1* | 12/2015 | Yaron | A61F 2/2466 |
| | | | | 623/2.36 |
| 2016/0287387 | A1* | 10/2016 | Wei | A61F 2/2454 |
| 2017/0252032 | A1 | 9/2017 | Hiorth et al. | |
| 2018/0146964 | A1* | 5/2018 | Garcia | A61B 17/00234 |
| 2018/0161035 | A1* | 6/2018 | Greenberg | A61F 2/2466 |
| 2018/0185153 | A1 | 7/2018 | Bishop et al. | |
| 2018/0271534 | A1* | 9/2018 | Shellenberger | A61B 17/122 |
| 2018/0296334 | A1* | 10/2018 | Dixon | A61F 2/2403 |
| 2018/0303614 | A1 | 10/2018 | Schaffner et al. | |
| 2018/0353181 | A1* | 12/2018 | Wei | A61F 2/2463 |
| 2019/0290260 | A1* | 9/2019 | Caffes | A61B 17/00234 |
| 2019/0358037 | A1 | 11/2019 | McAfee et al. | |
| 2020/0229806 | A1* | 7/2020 | Goldfarb | A61B 17/0625 |
| 2020/0375741 | A1* | 12/2020 | Cousins | A61B 17/068 |
| 2020/0383782 | A1* | 12/2020 | Basude | A61F 2/246 |
| 2021/0000597 | A1 | 1/2021 | Shuey et al. | |
| 2021/0000598 | A1 | 1/2021 | Shuey et al. | |
| 2021/0000599 | A1* | 1/2021 | Shuey | A61F 2/2457 |
| 2021/0007751 | A1* | 1/2021 | Shellenberger | A61B 17/1285 |
| 2021/0007847 | A1 | 1/2021 | Eggert et al. | |
| 2021/0022850 | A1* | 1/2021 | Basude | A61F 2/2463 |
| 2021/0128159 | A1* | 5/2021 | Taylor | A61B 17/1222 |
| 2021/0169651 | A1* | 6/2021 | Eggert | A61F 2/246 |
| 2021/0361416 | A1* | 11/2021 | Stearns | A61F 2/2466 |
| 2022/0039943 | A1* | 2/2022 | Phan | A61F 2/2466 |
| 2022/0096235 | A1 | 3/2022 | Giese et al. | |
| 2022/0226117 | A1* | 7/2022 | Colli | A61B 17/0401 |
| 2022/0287841 | A1* | 9/2022 | Freschauf | A61F 2/2466 |
| 2022/0313433 | A1* | 10/2022 | Ma | A61F 2/2436 |
| 2023/0020981 | A1* | 1/2023 | Giese | A61F 2/246 |
| 2023/0062599 | A1* | 3/2023 | Walker | A61B 17/0401 |
| 2023/0149170 | A1* | 5/2023 | Giese | A61B 17/1227 |
| | | | | 623/2.11 |
| 2023/0404565 | A1* | 12/2023 | Shuey | A61F 2/2457 |
| 2023/0404596 | A1* | 12/2023 | Shuey | A61B 17/1285 |
| 2024/0008983 | A1* | 1/2024 | Zhang | A61F 2/2466 |
| 2024/0108322 | A1* | 4/2024 | Chen | A61B 17/0057 |
| 2024/0156598 | A1* | 5/2024 | Oliver | A61F 2/2466 |
| 2024/0197475 | A1* | 6/2024 | Salsac | A61F 2/246 |
| 2024/0261103 | A1* | 8/2024 | Wang | A61F 2/2466 |
| 2024/0268957 | A1* | 8/2024 | Abunassar | A61F 2/2466 |
| 2024/0415652 | A1* | 12/2024 | Stearns | A61F 2/2466 |
| 2024/0423797 | A1* | 12/2024 | Oberwise | A61B 18/18 |
| 2025/0000653 | A1* | 1/2025 | O'Connor | A61F 2/246 |
| 2025/0025301 | A1* | 1/2025 | Weigler | A61F 2/246 |
| 2025/0073034 | A1* | 3/2025 | Abunassar | A61F 2/2466 |

* cited by examiner

DEVICES, SYSTEMS, AND METHODS FOR CLAMPING A LEAFLET OF A HEART VALVE

CROSS-REFERENCE TO RELATED APPLICATIONS

This application claims the benefit of priority of U.S. Provisional Application No. 63/239,467, filed Sep. 1, 2021, the entire disclosure of which is hereby incorporated by reference herein for all purposes.

FIELD

The present disclosure relates generally to the field of implantable medical devices. In particular, the present disclosure relates to medical devices, systems, and methods for cardiac treatment. More particularly, the present disclosure relates to medical devices, systems, and methods for coupling a leaflet clip to a heart valve, such as to deliver and implant artificial chordae tendineae in a heart.

BACKGROUND

Heart disease, including atrioventricular heart valve malfunctions, impedes patient cardiac output, which reduces patient quality of life and lifespan. The proper flow of blood through the heart is regulated, inter alia, by heart valves, including atrioventricular heart valves, which include soft tissue leaflets which cyclically open and close to allow blood to flow through in one direction. Healthy leaflets prevent blood flow in the opposite direction (regurgitation). Chordae tendineae, extending from the leaflets to the papillary muscles, support the proper functioning of the leaflets, such as by distributing load to the papillary muscles during systolic closure, and by preventing the leaflet from flailing into the atrium. As heart disease progresses, the chordae tendineae that connect the papillary muscle of the ventricle to a valve leaflet may stretch inelastically and may rupture. Various defects or failure or other improper functioning of the chordae tendineae, such as elongation, rupture, thickening, retraction, calcification, inelastic stretching, or other changes in elasticity, etc., may result in improper closure (e.g., sealing) of the heart valve and/or a flailing leaflet that may no longer have the capacity to form a valving seal for normal heart function. Abnormal blood flow regurgitation from the ventricle to the atrium may develop, preventing an adequate supply of blood to be delivered through the cardiovascular systems.

Heart valve disease is typically repaired via invasive surgical intervention or by complicated pinching of the leaflets together creating dual, smaller openings, or a replacement of the native valve. These approaches involve risky by-pass surgery that may include an opening into the patient's chest and heart chamber to expose the heart valve for direct viewing and repair.

Resection, partial removal, and/or repair of the patient's leaflets along with the implantation of a surgical ring are complex techniques used by surgeons to reduce the diameter of the patient's heart valve annulus, thus allowing the leaflets to properly coapt and reduce regurgitate flow. Some techniques may slightly reduce regurgitate flow but may not provide a durable solution and do not repair and/or replace damaged chordae tendineae of a valve. Thus, transluminal solutions to mitral valve disease are needed.

There is a need for minimally invasive solutions for tissue clips and/or for delivering and deploying a tissue clip, such as to repair a heart valve, such as the leaflets thereof, while maintaining the option for future interventions.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a leaflet clip delivery and deployment system includes a clip spreader having an atrial spreader arm and a ventricular spreader arm, and a leaflet clip having an atrial clip arm and a ventricular clip arm. The atrial spreader arm and the atrial clip arm have mating atrial retention elements configured to retain the atrial spreader arm and the atrial clip arm together. The ventricular spreader arm and the ventricular clip arm have mating ventricular retention elements configured to retain the ventricular spreader arm and the ventricular clip arm together. At least one of the mating atrial retention elements or the mating ventricular retention elements are configured for sliding engagement and disengagement.

In some embodiments, at least one of the atrial retention element of the atrial clip arm or the ventricular retention element of the ventricular clip arm includes an aperture. In some embodiments, the ventricular retention element of the ventricular spreader arm includes a hook configured to engage within a ventricular retention element of the ventricular clip arm in the form of an aperture, and to disengage from the aperture by a sliding movement. In some embodiments, the leaflet clip is disengaged from the clip spreader by relative distal sliding movement of the ventricular retention element of the ventricular spreader arm or proximal sliding movement of the ventricular retention element of the ventricular clip arm. In some embodiments, the atrial retention element of the atrial spreader arm includes a boss configured to mate within an atrial retention element of the atrial clip arm in the form of an aperture, and, optionally, the atrial retention element further includes a movable retention element in the form of a wire shiftable between an engaged position engaged with the boss to maintain the atrial spreader arm and the atrial clip arm engaged, and a disengaged position disengaged from the boss and allowing the atrial spreader arm and the atrial clip arm to disengage from each other as a result of relative movement therebetween.

In some embodiments, the atrial retention element of the atrial spreader arm includes a boss configured to mate within an atrial retention element of the atrial clip arm in the form of an aperture, and the atrial retention element further includes a movable retention element shiftable between an engaged position maintaining the atrial spreader arm and the atrial clip arm engaged, and a disengaged position allowing the atrial spreader arm and the atrial clip arm to disengage from each other as a result of relative movement therebetween. In some embodiments, the movable retention element is shiftable between an engaged position engaged with the boss and a disengaged position disengaged from the boss.

In some embodiments, the clip spreader has a recess configured to accommodate a flex zone of a leaflet clip about which the atrial clip arm and the ventricular clip arm of the leaflet clip move between an open configuration for accepting tissue therebetween and a closed configuration for clamping onto tissue.

In some embodiments, the clip spreader includes a pivot between the atrial spreader arm and the ventricular spreader arm, the leaflet clip includes a flex zone between the atrial clip arm and the ventricular clip arm, the flex zone biases the atrial clip arm and the ventricular clip arm into a closed configuration for clamping onto tissue and flexes to allow the atrial clip arm and the ventricular clip arm to move apart from each other, the atrial clip arm and the ventricular clip arm and the flex zone hold the atrial spreader arm and the ventricular spreader arm in a closed configuration, and the leaflet clip delivery and deployment systems further comprise a clip spreader actuator having a distal end coupled to the ventricular spreader arm at a coupling point, the clip spreader actuator extending distally from the coupling point, around the clip spreader, proximally along the ventricular spreader arm, and proximally to a proximal end thereof.

In accordance with various principles of the present disclosure, a leaflet clip is configured to engage a clip spreader slidably. In some aspects, the leaflet clip includes an atrial clip arm, a ventricular clip arm, and a flex zone between the atrial clip arm and the ventricular clip arm, the flex zone biasing the atrial clip arm and the ventricular clip arm into a closed configuration for clamping onto tissue, and flexing to allow the atrial clip arm and the ventricular clip arm to move apart from each other, where at least one of the atrial clip arm and the ventricular clip arm is configured for sliding engagement and disengagement with a clip spreader configured to move the atrial clip arm and the ventricular clip arm apart from each other.

In some embodiments, an aperture is defined in at least one of the atrial clip arm or the ventricular clip arm, the aperture configured for sliding engagement and disengagement with a clip spreader configured to move the atrial clip arm and the ventricular clip arm apart from each other.

In some embodiments, the flex zone extends outwardly away from only one of the atrial clip arm and the ventricular clip arm.

In some embodiments, one of the atrial clip arm and the ventricular clip arm includes projections in the form of teeth, the other of the atrial clip arm and the ventricular clip arm includes projections in the form of bumps, and the teeth and bumps cooperate to engage tissue between the atrial clip arm and the ventricular clip arm.

In some embodiments, cuts are formed in at least one of the atrial clip arm and the ventricular clip arm, and portions of the at least one of the atrial clip arm and the ventricular clip arm are bent along the cuts to form teeth for engaging tissue.

In some embodiments, a method of deploying a leaflet clip, having an atrial clip arm and a ventricular clip arm coupled together by a flex zone, includes slidably engaging at least one of the atrial clip arm or the ventricular clip arm with a corresponding atrial spreader arm or ventricular spreader arm of a clip spreader, deploying the leaflet clip to clamp onto another element, and slidably moving the leaflet clip and the clip spreader relative to each other to cause the at least one of the atrial clip arm or the ventricular clip arm to release from the clip spreader.

In some embodiments, the method further includes clamping the leaflet clip onto a leaflet, and allowing movement of the leaflet to slide the leaflet clip off the clip spreader. In some embodiments, the method further includes extending an artificial chordae tendineae from the leaflet clip to a ventricle wall, moving components associated with the artificial chordae tendineae away from the deployment site of the leaflet clip and into a commissure or cleft of the leaflet, adjusting tension on the artificial chordae tendineae, and observing the functioning of the leaflet. In some embodiments, the ventricular clip arm is slidably engaged with the ventricular spreader arm such that movement of a leaflet clamped between the atrial clip arm and the ventricular clip arm slides the ventricular clip arm out of engagement with the ventricular spreader arm.

In some embodiments, the method further includes clamping the leaflet clip onto a leaflet, distally advancing the clip spreader with respect to the clamped leaflet to slidingly disengage the leaflet clip and the clip spreader.

In some embodiments, the method further includes moving the atrial clip arm and the ventricular clip arm apart from each other by actuating an actuator to move the atrial spreader arm and the ventricular spreader arm apart from each other.

The leaflet clip delivery and deployment system may also include where the ventricular retention element of the ventricular spreader arm includes a hook configured to engage within a ventricular retention element of the ventricular clip arm in the form of an aperture, and to disengage from the aperture by a sliding movement.

The leaflet clip delivery and deployment system may also include where the leaflet clip is disengaged from the clip spreader by relative distal sliding movement of the ventricular retention element of the ventricular spreader arm or proximal sliding movement of the ventricular retention element of the ventricular clip arm.

The leaflet clip delivery and deployment system may also include where the atrial retention element of the atrial spreader arm includes a boss configured to mate within an atrial retention element of the atrial clip arm in the form of an aperture, and the atrial retention element further includes a movable retention element in the form of a wire shiftable between an engaged position engaged with the boss to maintain the atrial spreader arm and the atrial clip arm engaged, and a disengaged position disengaged from the boss and allowing the atrial spreader arm and the atrial clip arm to disengage from each other as a result of relative movement therebetween.

The leaflet clip delivery and deployment system may also include where the atrial retention element further includes a movable retention element shiftable between an engaged position maintaining the atrial spreader arm and the atrial clip arm engaged, and a disengaged position allowing the atrial spreader arm and the atrial clip arm to disengage from each other as a result of relative movement therebetween.

The leaflet clip delivery and deployment system may also include where the atrial retention element of the atrial spreader arm includes a boss configured to mate within an atrial retention element of the atrial clip arm in the form of an aperture.

The leaflet clip delivery and deployment system may also include where the movable retention element is shiftable between an engaged position engaged with the boss and a disengaged position disengaged from the boss.

The method may also include where the ventricular clip arm is slidably engaged with the ventricular spreader arm such that movement of a leaflet clamped between the atrial clip arm and the ventricular clip arm slides the ventricular clip arm out of engagement with the ventricular spreader arm. Other technical features may be readily apparent to one skilled in the art from the following figures, descriptions, and claims.

In accordance with various principles of the present disclosure, an actuator for a clip spreader may be provided in combination with the above-described features or independently (without such features).

In some embodiments, a leaflet clip includes projections in the form of bumps. A leaflet clip may be provided with such projections independently of (i.e., without) the other above-described features.

It will be appreciated that actuation of a clip spreader with a clip spreader actuator may be performed without the above-described sliding engagement of the leaflet clip and clip spreader. The clip spreader may be used to reopen the leaflet clip after the leaflet clip has already been opened and closed by the clip spreader, such to reposition the leaflet clip or to bail out a leaflet clip delivery and deployment system from being too close to chordae tendineae at the deployment site.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary.

For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements of illustrated leaflet clips are typically designated with similar reference numbers differing in increments of 1000, with redundant description omitted.

Figure 1:
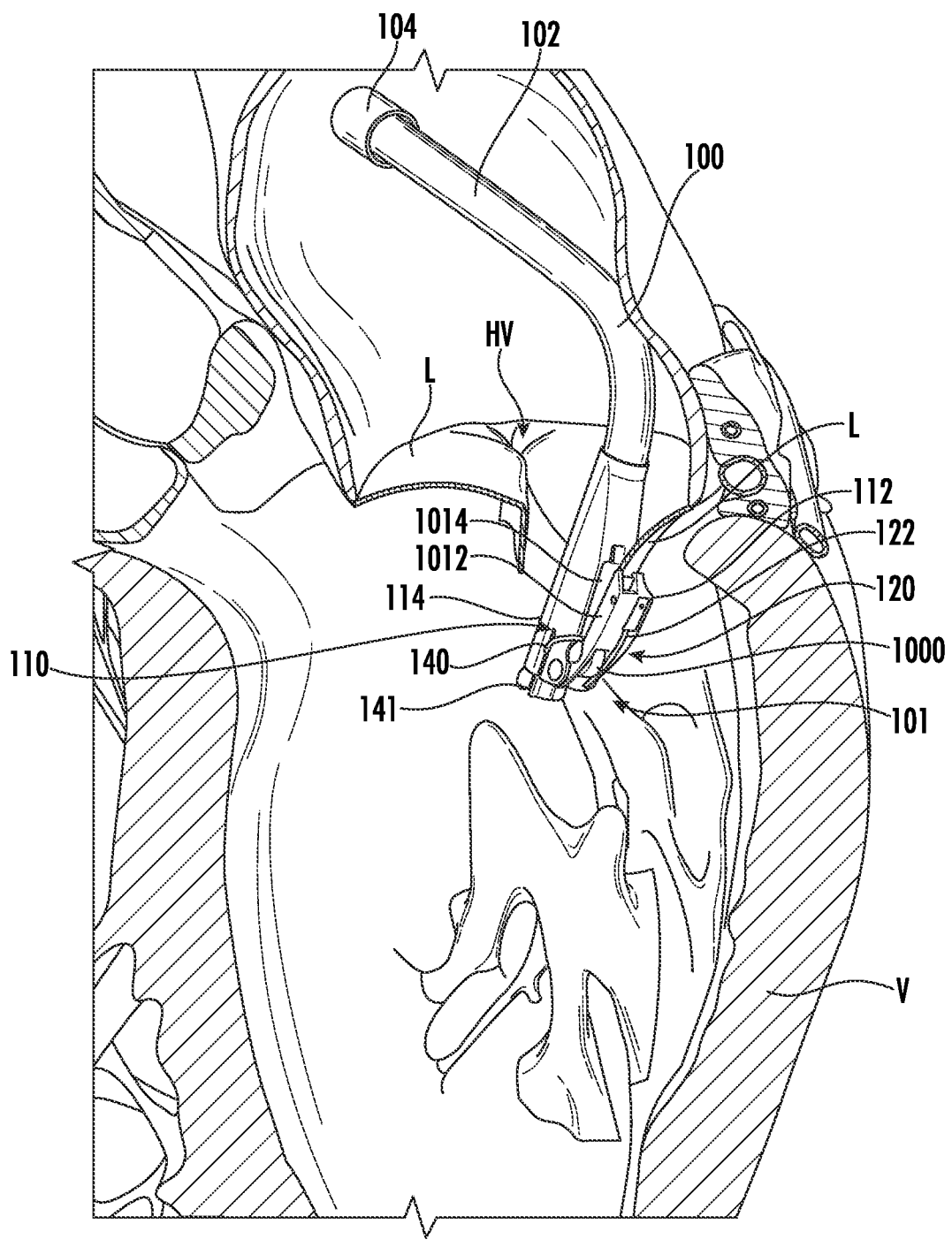

For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 1 illustrates a perspective view of an example of an embodiment of a leaflet clip system formed in accordance with various principles of the present disclosure positioned to deploy a clip with respect to a schematic representation of a heart valve leaflet.

Figure 2:
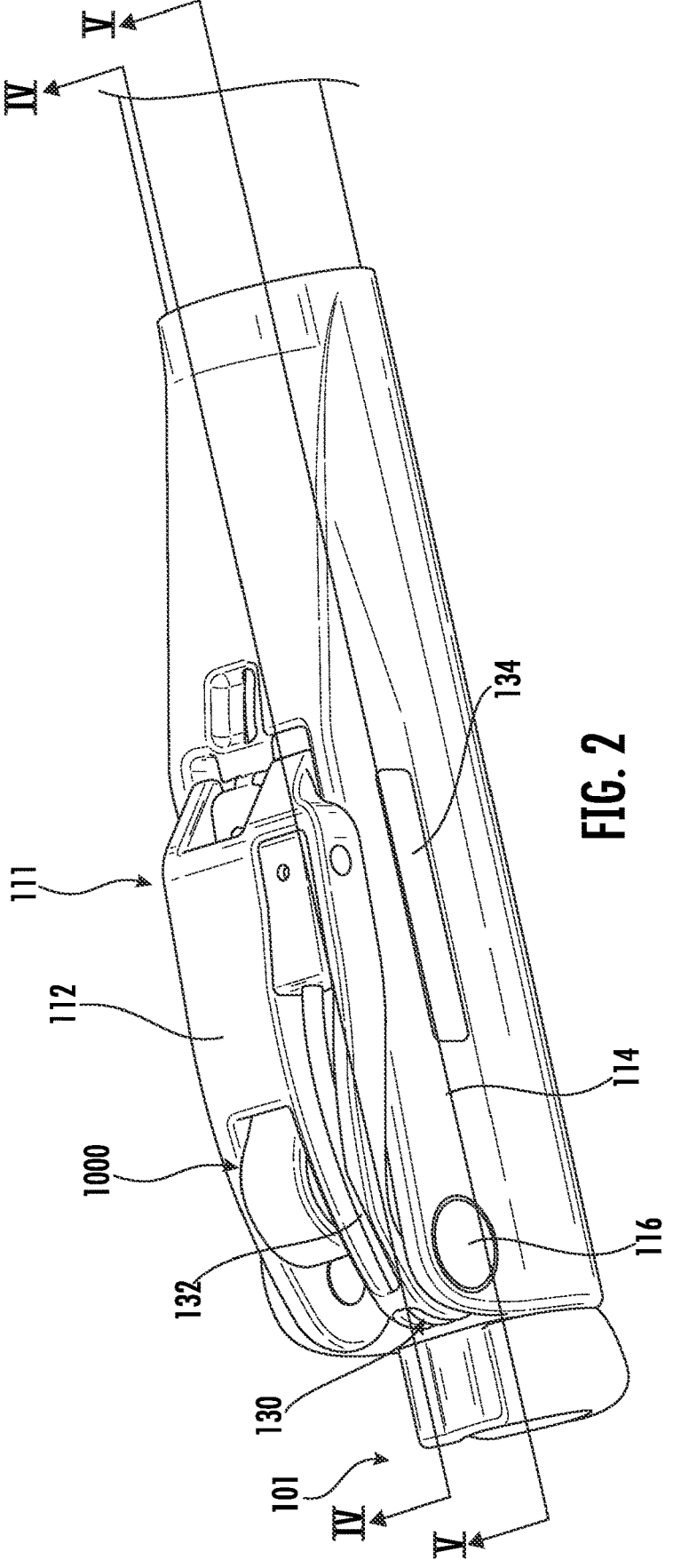

FIG. 2 illustrates a perspective view of an example of an embodiment of a leaflet clip system formed in accordance with various principles of the present disclosure positioned to deploy a clip with respect to a schematic representation of a heart valve leaflet.

Figure 3:
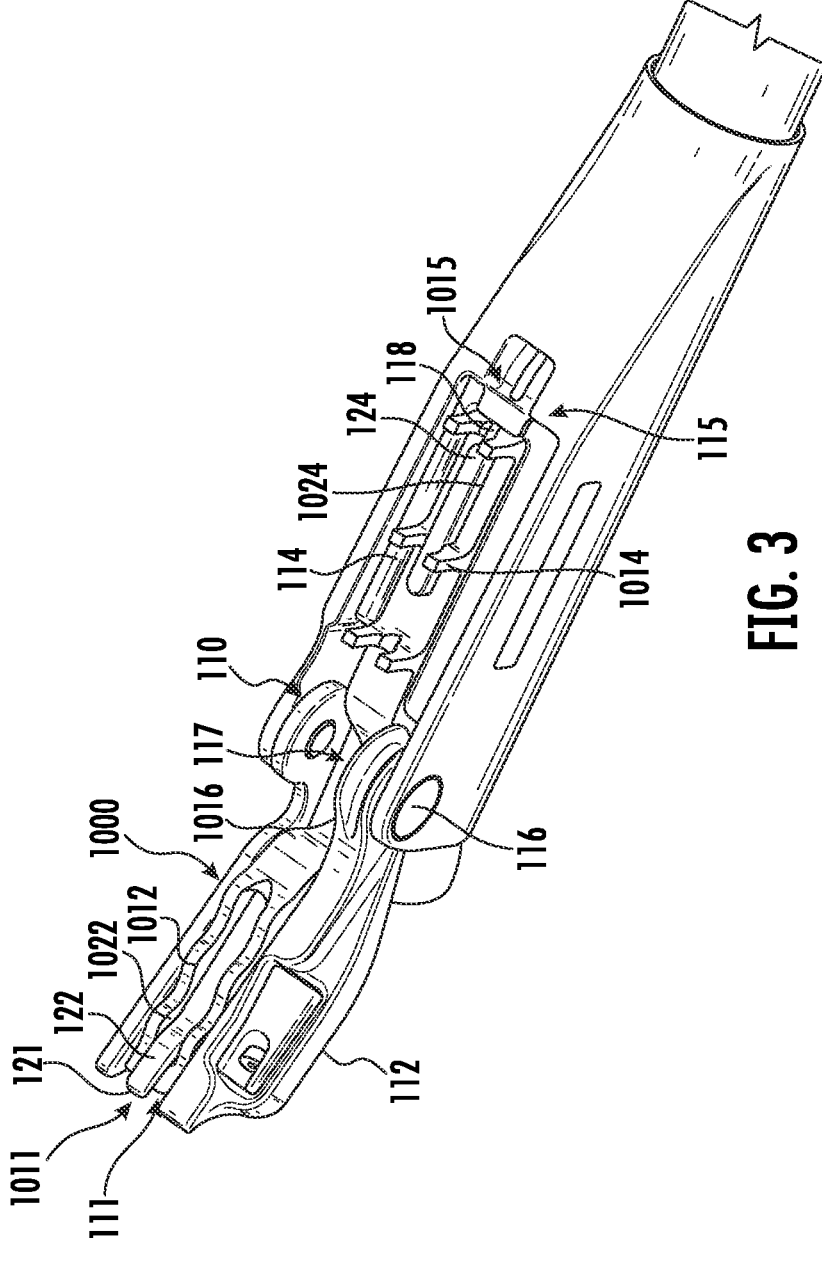

FIG. 3 illustrates a perspective view showing the clip spreader of a leaflet clip system as in FIG. 2 opening an example of an embodiment of a leaflet clip.

6

Figure 4:
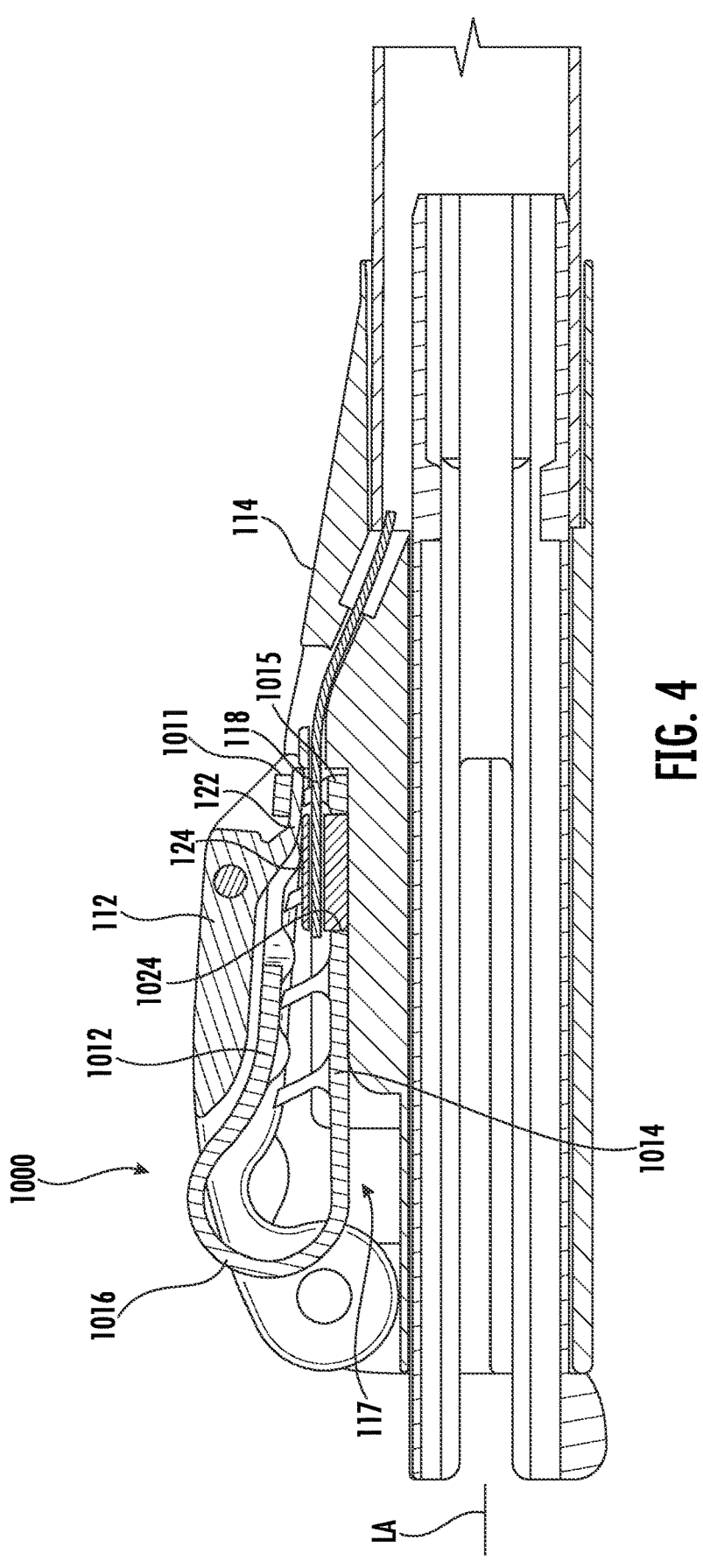

FIG. 4 illustrates a cross-sectional view along line IV-IV of a leaflet clip system as in FIG. 2 showing clip retention components.

Figure 5:
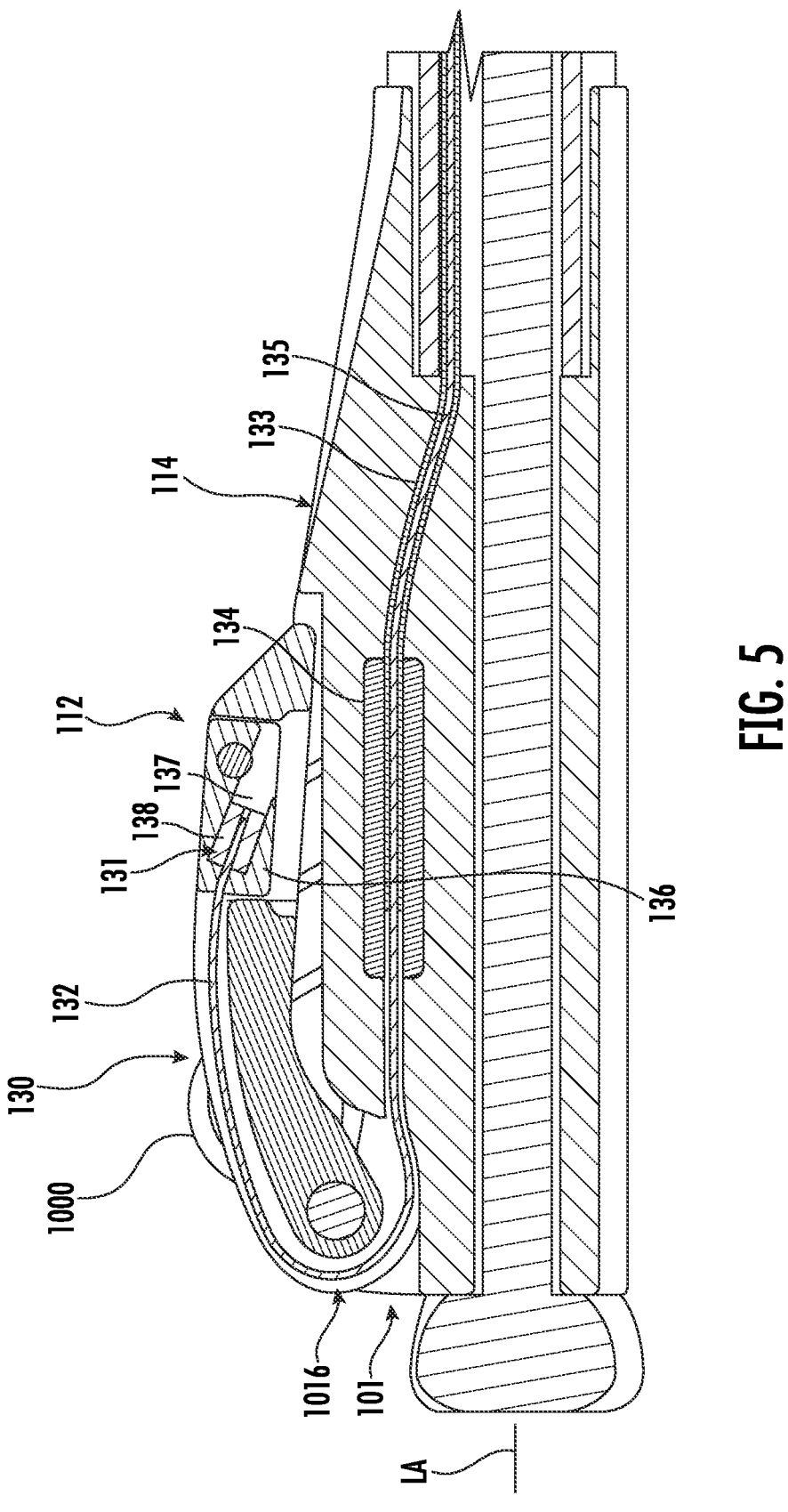

FIG. 5 illustrates a cross-sectional view along line V-V of a leaflet clip system as in FIG. 2 showing a clip spreader actuator.

Figure 6:
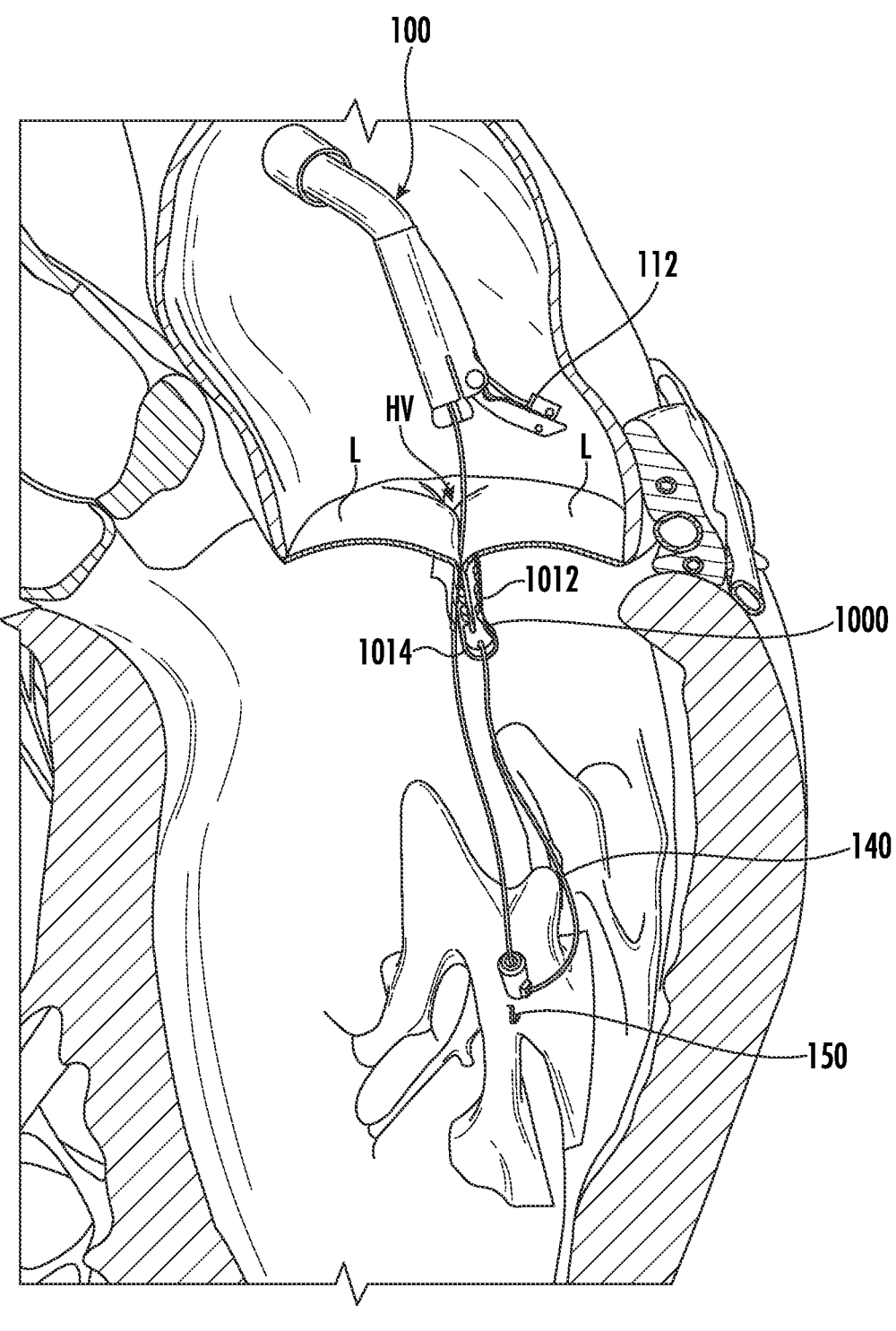

FIG. 6 illustrates a schematic representation of a heart with an example of an embodiment of a leaflet clip formed in accordance with various principles of the present disclosure and attached to a heart valve leaflet and with an artificial chordae tendineae extending therefrom and anchored to the heart.

Figure 7:
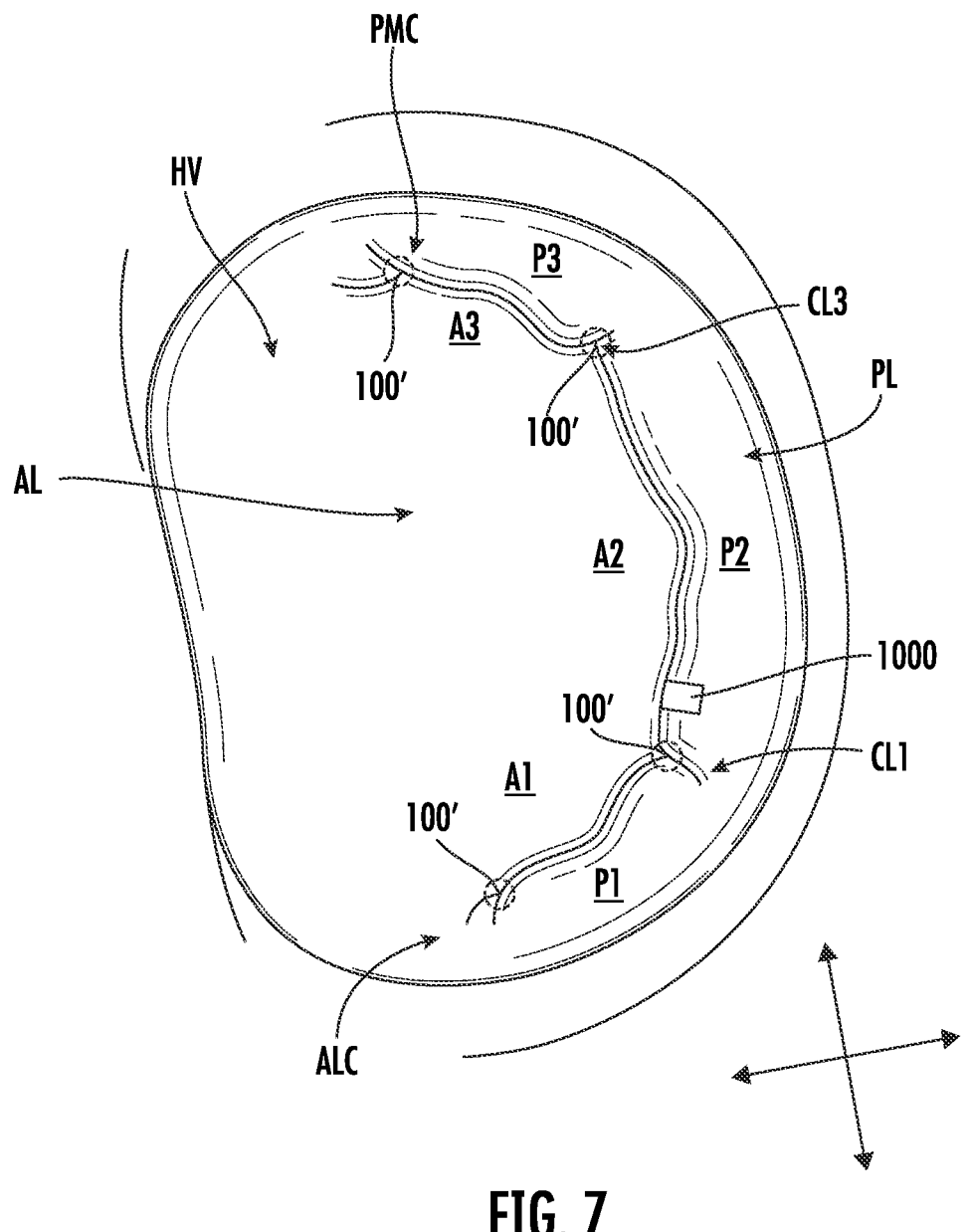

FIG. 7 illustrates a schematic plan view of a heart being treated in accordance with various principles of the present disclosure.

Figure 8:
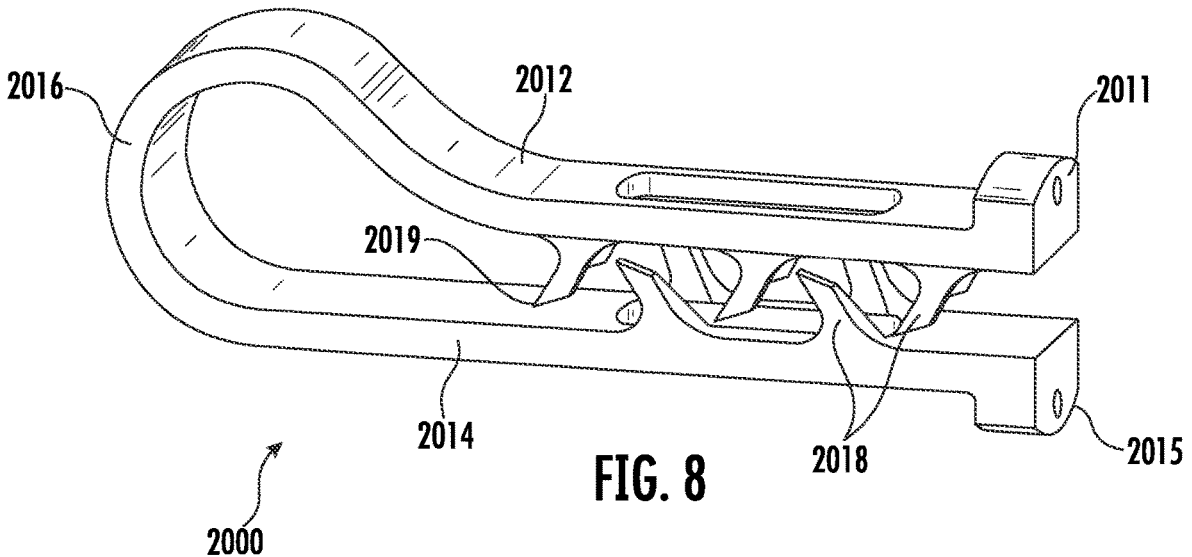

FIG. 8 illustrates a perspective view of an example of an embodiment of a leaflet clip formed in accordance with various principles of the present disclosure.

Figure 9:
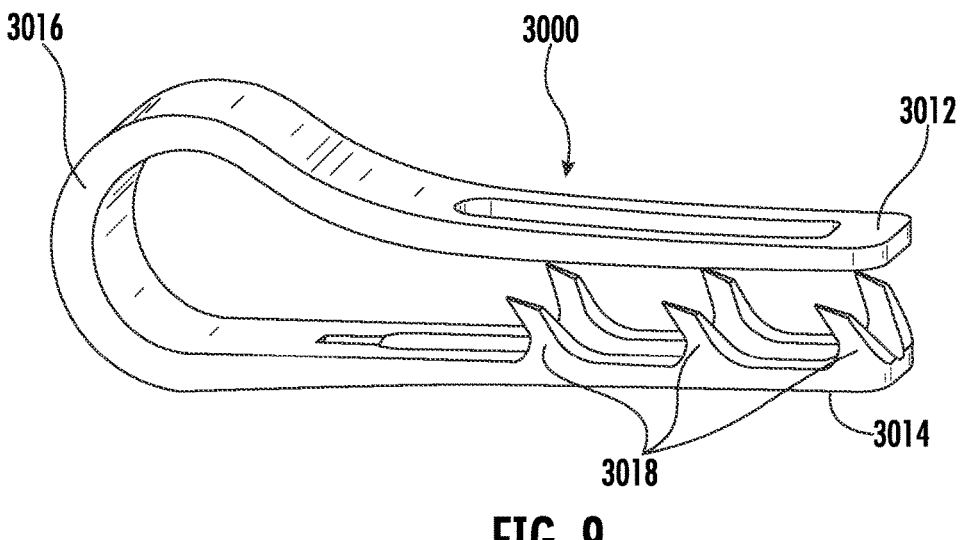

FIG. 9 illustrates a perspective view of an example of an embodiment of a leaflet clip formed in accordance with various principles of the present disclosure.

Figure 10:
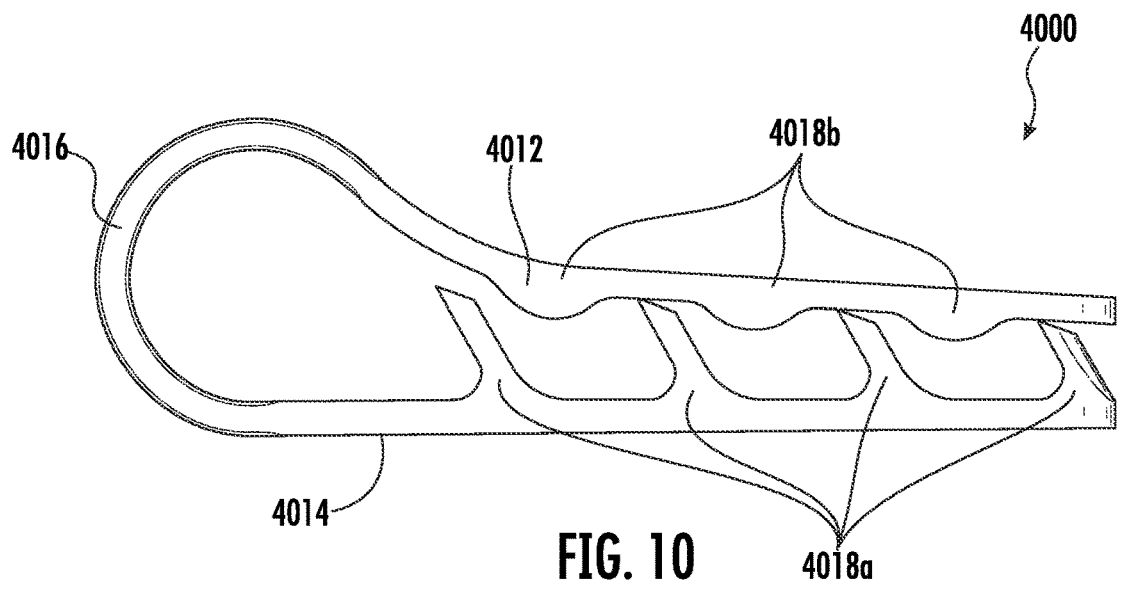

FIG. 10 illustrates a perspective view of an example of an embodiment of a leaflet clip formed in accordance with various principles of the present disclosure.

Figure 11:
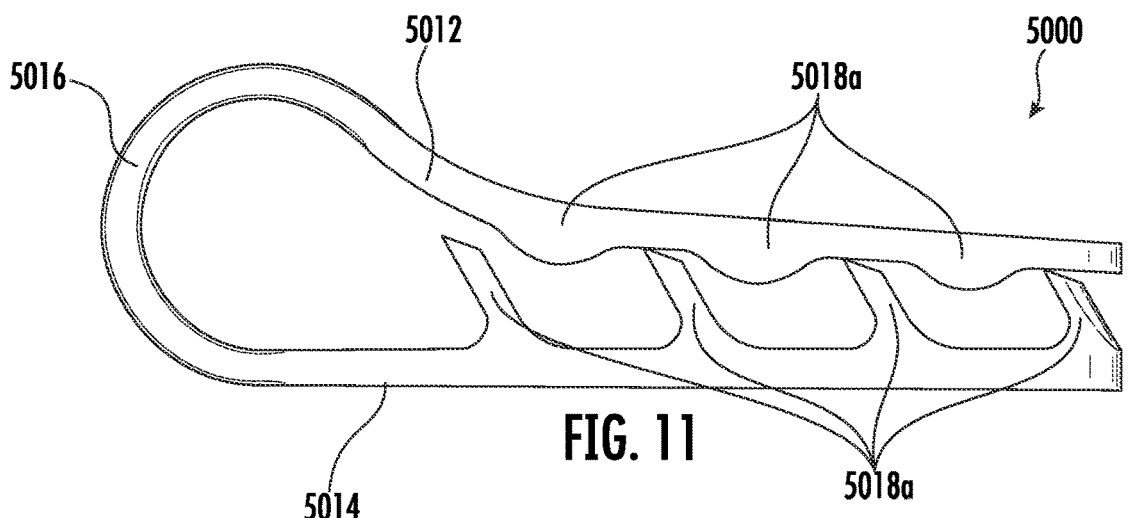

FIG. 11 illustrates an elevational view of an example of an embodiment of a leaflet clip formed in accordance with various principles of the present disclosure.

Figure 12:
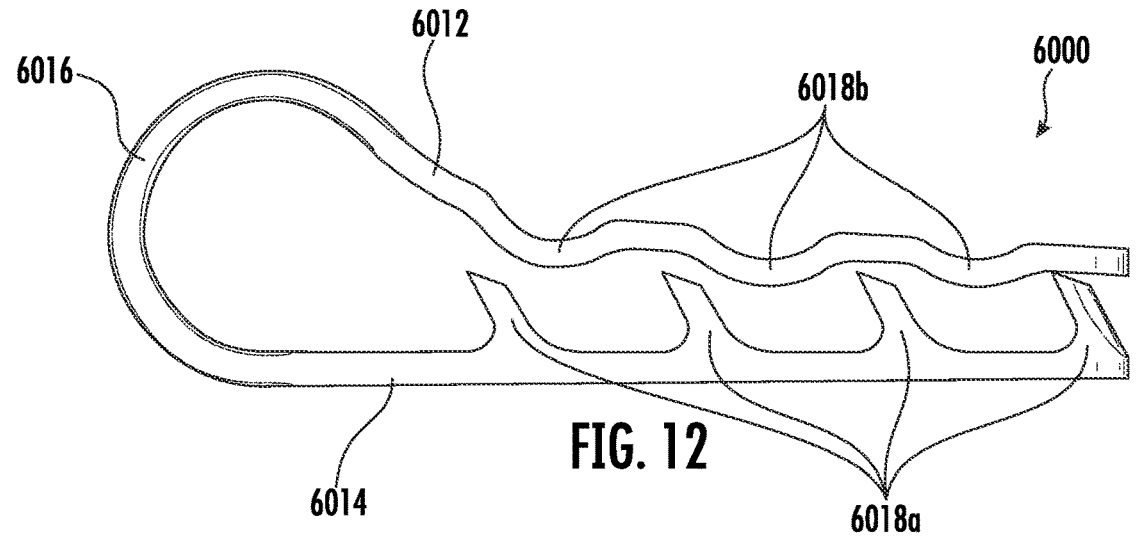

FIG. 12 illustrates an elevational view of an example of an embodiment of a leaflet clip formed in accordance with various principles of the present disclosure.

Figures 13, 14, 15:
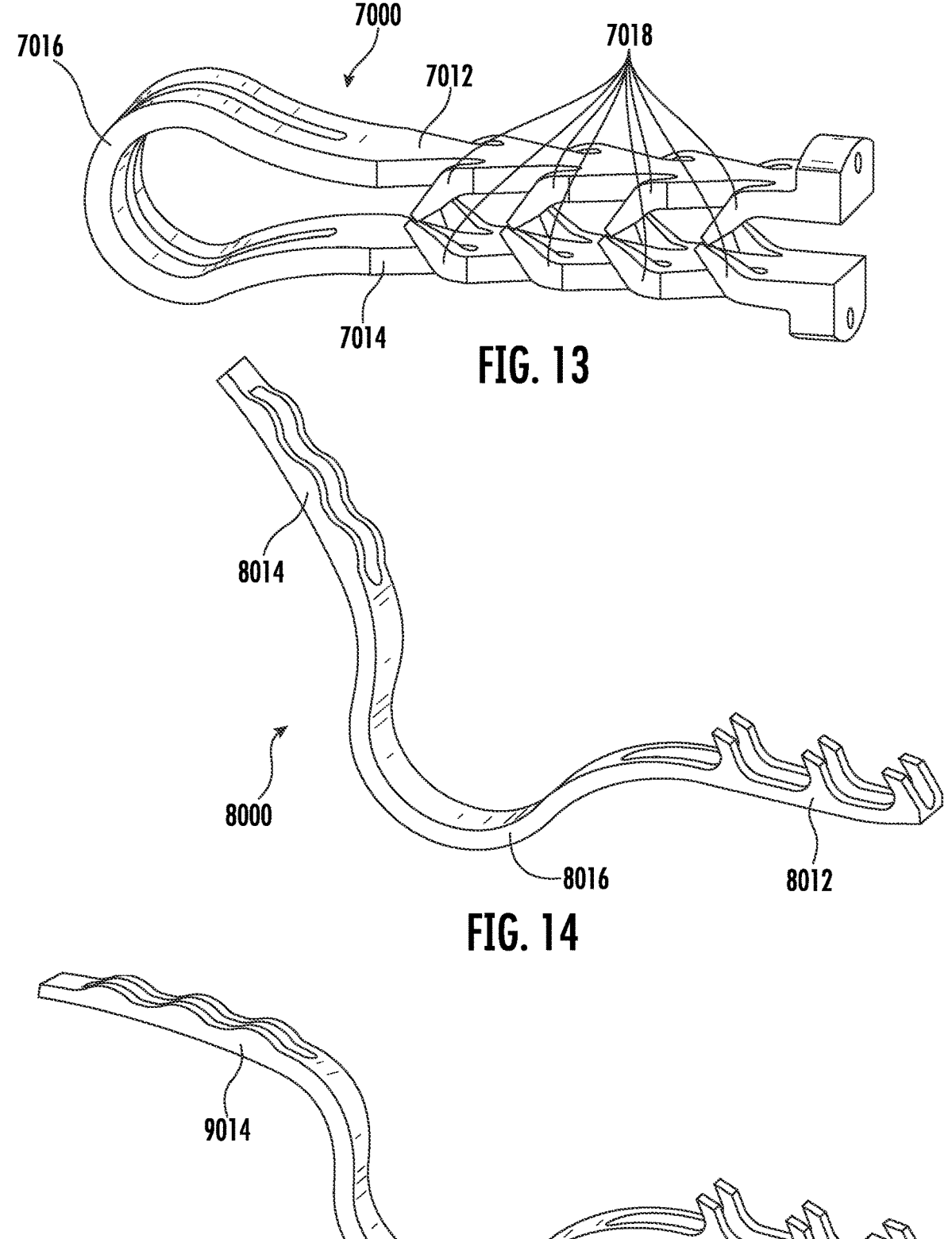

FIG. 13 illustrates an elevational view of an example of an embodiment of a leaflet clip formed in accordance with various principles of the present disclosure.

FIG. 14 illustrates a perspective view of the example of an embodiment of a leaflet clip formed in accordance with various principles of the present disclosure in an open configuration.

FIG. 15 illustrates a perspective view of the example of an embodiment of a leaflet clip formed in accordance with various principles of the present disclosure in a further open configuration.

DETAILED DESCRIPTION

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point and/or generally equidistant from a periphery or boundary, and a "central axis" means, with respect to an opening, a line that at least generally bisects a center point of the opening, extending longitudinally along the length of the opening when the opening comprises, for example, a tubular element, a channel, a cavity, or a bore. It will be appreciated that a "bore" is not limited to a circular cross-section. As used herein, a "free end" of an element is a terminal end at which such element does not extend beyond.

Repositioning, repair, and/or replacement of one or more leaflets of a valve and/or chordae tendinea may be desirable to treat heart disease. The devices, systems, and methods of the present disclosure may be used alone or together with other devices, systems, and methods to treat heart disease. Examples of devices, systems, and methods with which embodiments of the present disclosure may be implemented include, but are not limited to, those described in U.S. Patent Application Publication US2021/0007847, titled Devices, Systems, And Methods For Clamping A Leaflet Of A Heart Valve, and published on Jan. 14, 2021; U.S. Patent Application Publication US2021/0000597, titled Devices, Systems, And Methods For Adjustably Tensioning An Artificial Chordae Tendineae Between A Leaflet And A Papillary Muscle Or Heart Wall, and published on Jan. 7, 2021; U.S. Patent Application Publication US2021/0000599, titled Devices, Systems, And Methods For Artificial Chordae Tendineae, and published on Jan. 7, 2021; U.S. Patent Application Publication US2021/0000598, titled Devices, Systems, And Methods For Anchoring An Artificial Chordae Tendineae To A Papillary Muscle Or Heart Wall, and published on Jan. 7, 2021; and U.S. Patent Application Publication 2022/0096235, filed on Sep. 23, 2021, titled Devices, Systems, And Methods For Adjustably Tensioning Artificial Chordae Tendineae In A Heart, and published on Mar. 31, 2022, each of which is herein incorporated by reference in its entirety and for all purposes. Examples of devices described therein may be modified to incorporate embodiments or one or more features of the present disclosure.

Repositioning, repair, and/or replacement of one or more leaflets of a valve and/or chordae tendinea may include one or more devices to be fixed to one or more leaflets of a heart valve. Examples of embodiments of devices and systems and methods described herein facilitate fixation of one or more devices to a heart valve by clamping the device to a leaflet. Examples of embodiments of devices and systems described herein may provide a fixed point for other devices, systems, or tools to grab or attach to in order to manipulate a leaflet of a valve and/or deliver devices attached to the leaflet. It will be appreciated that devices and systems described herein may be used with any of the devices or systems disclosed in the above-referenced applications incorporated herein, or may be used with other devices and systems, such as those described herein.

In accordance with various principles of the present disclosure, a leaflet clip delivery and deployment system as described herein includes a clip spreader configured to deliver and deploy a leaflet clip configured to be clipped onto a heart valve leaflet. It will be appreciated that terms such as clip, clamp, clasp, couple, engage, attach, deploy on, grasp, hold, etc. (including other grammatical forms thereof) may be used interchangeably herein, such as with reference to the interaction of the clip and tissue engaged by the clip, without intent to limit. The leaflet clip delivery and deployment system may include a leaflet clip configured to be delivered and deployed by the clip spreader. The leaflet clip may be biased into a closed configuration, such as to clamp tissue. In one aspect, the clip spreader is configured to actuate the leaflet clip (whether or not included with the system or provided separately) into a configuration for placement with respect to a heart valve leaflet. For instance, a leaflet clip may have first and second arms coupled together via a flex zone which may bias the leaflet clip arms together. The clip spreader may be configured to move (e.g., spread) the first and second arms of the leaflet clip apart into an open configuration. The clip spreader may be further configured to release the leaflet clip to clamp onto a heart valve leaflet. For instance, release of the leaflet clip from the clip spreader may allow the arms of the leaflet clip to return to a closed configuration permitting clamping of tissue therebetween. Further, in some embodiments, the clip spreader is configured to reopen a leaflet clip that has been released to clamp onto a heart valve leaflet before release of the leaflet clip from the clip spreader if repositioning of the leaflet clip is desired. The spreader arms of the clip spreader and the leaflet clip arms may be coupled together to move together. As such, actuation of the clip spreader arms to move apart causes the leaflet clip arms to move apart. The leaflet clip arms may be biased into a closed configuration (close to each other to clamp onto tissue) so that release of an actuating force on the clip spreader arms allows the leaflet clip arms to return to a closed position, also returning the clip spreader arms to return to a closed position.

In accordance with an aspect of the present disclosure, a clip spreader and a leaflet clip formed in accordance with various principles of the present disclosure may be configured so that the clip spreader and the leaflet clip are engaged (e.g., coupled together) for delivery of the leaflet clip to a deployment site (e.g., a selected position on a heart valve leaflet), and to facilitate release of the leaflet clip from the clip spreader once at the deployment site, and, optionally, engaged with tissue (e.g., a heart valve leaflet) at the deployment site. More particularly, in some embodiments, a clip spreader and a leaflet clip may be configured to be slidingly engaged with each other. In such embodiments, the leaflet clip may be readily released from the clip spreader by relative movement between the leaflet clip and the clip spreader. In other words, in some embodiments, relative movement, such as relative sliding movement, between the leaflet clip and the clip spreader results in or causes engagement or disengagement of the leaflet clip and the clip spreader. In some embodiments, the relative movement is in a single direction, such as a sliding movement, such as along a longitudinal axis. In some embodiments, further actions beyond such relative movement in such embodiments are not necessary. Actuation of a further element to permit such relative movement between the clip spreader and the leaflet clip may not be necessary. Movement of the heart valve leaflet to which the leaflet clip is clamped may move the leaflet clip with respect to the clip spreader to remove from the clip spreader to deploy the leaflet clip.

In some embodiments, an additional retention element is provided to hold at least a portion of the leaflet clip with respect to the clip spreader until the leaflet clip is ready for deployment and release from the clip spreader. For instance, a retention element may interact with a portion of the leaflet clip and the clip spreader to retain the leaflet clip in position with respect to the clip spreader, such as in a delivery position. The retention element may be configured to be readily actuated to release the leaflet clip from the clip spreader. For instance, the retention element may be slidable with respect to the leaflet clip and/or the clip spreader to permit release of the leaflet clip from the clip spreader. In some embodiments, the leaflet clip has a first arm and a second arm, and the retention element is associated with one of the leaflet clip arms, and the other of the leaflet clip arms may be engaged with the clip spreader in a manner as described above to facilitate release of the leaflet clip from the clip spreader simply by relative sliding movement therebetween without actuation of another element. The retention element may block the leaflet clip from moving with respect to the clip spreader until the retention element is moved to a release position.

In accordance with a separate and independent aspect of the present disclosure, a leaflet clip delivery and deployment system formed in accordance with various principles of the present disclosure includes a clip spreader actuator coupled with a portion of the clip spreader to actuate the clip spreader to actuate a leaflet clip to shift between a closed configuration and an open configuration. The leaflet clip actuator is configured and coupled with the leaflet clip delivery and deployment system to allow a medical professional to control the clip spreader, such as based on the position of the leaflet clip delivery and deployment system with respect to a deployment site. The leaflet clip delivery and deployment system may be delivered at a distal end of a delivery shaft. The clip spreader actuator may be coupled to a portion of the clip spreader and extend proximally from the distal end of the delivery shaft to a position (e.g., along a proximal end of the delivery shaft) at which a medical professional may control the clip spreader actuator as desired. The clip spreader actuator may be pulled (at the proximal end thereof) to actuate the clip spreader, and released (or tension reduced) to allow the clip spreader to be returned to a closed position (e.g., by spring forces of the leaflet clip coupled thereto). The clip spreader actuator may be coupled to the clip spreader in a manner which improves upon prior application of force vectors to prior clip spreaders. For instance, a clip spreader actuator formed in accordance with various principles of the present disclosure may be coupled to a clip spreader arm to be directed away from the open tissue-engaging side of the leaflet clip and extend toward a pivot about which arms of the clip spreader are coupled. Additionally or alternatively, a clip spreader actuator formed in accordance with various principles of the present disclosure may be positioned and/or oriented so that it does not interfere with clamping of the leaflet clip onto body tissue. Additionally or alternatively, a clip spreader actuator formed in accordance with various principles of the present disclosure may be positioned and/or oriented so that it does not interfere with release of the leaflet clip from the clip spreader. Additionally or alternatively, the clip spreader actuator may be coupled to the clip spreader in a manner which permits the clip to be oriented to facilitate deployment, and, optionally, to facilitate release from the clip spreader.

In accordance with yet another separate and independent aspect of the present disclosure, a leaflet clip delivery and deployment system may be configured with a flex region to accommodate flexing of a leaflet clip from a closed configuration to an open configuration. In some embodiments, a leaflet clip delivery and deployment system formed in accordance with various principles of the present disclosure includes a clip spreader having a flex region configured to accommodate flexing of a leaflet clip from a closed configuration to an open configuration. The flex region may include a widened area or opening to allow a flex zone of a leaflet clip to flex into the flex region.

It will be appreciated that a leaflet clip delivery and deployment system may be formed in accordance with various principles of the present disclosure to accommodate various configurations of leaflet clips. Embodiments of leaflet clips described herein include various features and structures formed in accordance with various principles of the present disclosure to enhance or otherwise improve the leaflet clips relative to prior leaflet clip.

In some embodiments, various of the disclosed leaflet clips include a first arm and a second arm coupled together by a flex zone. The flex zone may bias the first and second leaflet clip arms into a closed configuration (close together such as to clamp onto tissue). The first and second leaflet arms are capable of moving apart from each other, such as by flexing the flex zone. It will be appreciated that the term moving (and various conjugations and other grammatical forms thereof) may be used interchangeably herein with terms such as spreading, separating, shifting, transitioning, etc., without intent to limit. It will further be appreciated that the term flexing (and various conjugations and other grammatical forms thereof) may be used interchangeably herein with terms such as bending, biasing, extending, deforming, straightening, etc., without intent to limit.

To facilitate opening (and optional opening, closing, and reopening) of a leaflet clip, it may be beneficial to extend the flex zone of the leaflet clip outwardly from a longitudinal axis of the leaflet clip arms to improve distribution of bending forces. For instance, various prior art leaflet clips include an enlarged or widened flex zone. However, it may also be desirable for the leaflet clip to have a generally compact outer dimension so as not to interfere with normal functioning of the anatomical site to which the clip is clamped. For instance, a leaflet clip clamped on a heart valve leaflet moves with the leaflet and optimally does not interfere with coaptation of the leaflets of the heart valve. In accordance with an aspect of the present disclosure, a leaflet clip formed in accordance with various principles of the present disclosure may be configured with an asymmetrical flex zone. More particularly, a leaflet clip formed in accordance with various principles of the present disclosure may include an atrial clip arm clipped on the side of a heart valve leaflet facing the atrium of the heart, a ventricular clip arm clipped on the side of the heart valve leaflet facing the ventricle of the heart, and a flex zone between the atrial clip arm and the ventricular clip arm. The flex zone may extend outwardly from only the ventricular clip arm (i.e., expanded from the ventricular clip arm away from the atrial clip arm), with the flex zone not extending (or insubstantially extending) beyond the atrial clip arm. A leaflet clip formed as such does not interfere with proper coaptation of a heart valve leaflet to which the leaflet clip is clamped with other heart valve leaflets.

It will be appreciated that a leaflet clip used with a leaflet clip delivery and deployment system as described herein generally may include one or more tissue engagement features configured to engage with body tissue to which the clip is to be clamped, such as to secure or enhance securement of the clip with the tissue. The tissue engagement features may be in the form of projections, such as teeth. The projections may be formed in any of a variety of manners in accordance with various principles of the present disclosure. For instance, the projections may be formed by machining (e.g., milling and/or wire electrical discharge machining (EDM)) or molding or heat forming or welding teeth onto at least one arm of the leaflet clip. More particularly, in some embodiments, a strip or rod of material (e.g., Nitinol) is machined by removing material in a series of steps until the desired profile (e.g., with the desired number and configuration and arrangement of projections) is formed. In some embodiments, the initial strip or rod of material is approximately ⅛ in (3.175 mm) thick. Additionally or alternatively, the projections may be formed by cutting/slitting material of leaflet clip (e.g., the leaflet clip arm) and bending a portion of the leaflet clip away from the adjacent portion to form a tissue engagement feature such as a projection or tooth. In accordance with various principles of the present disclosure, one or more of the tissue engagement features on a first arm of a leaflet clip may be curved features, such as in the form of bumps, which enhance purchase of the tissue between the first arm and a second arm. For instance, curved tissue engagement features on a first arm may be configured to displace tissue towards a second arm of leaflet clip. The second arm may have tissue engagement features which are curved, such as bumps, or a sharper configuration, such as teeth. In some embodiments, curved tissue engagement features are gently curved so as not to catch onto other anatomical features, as may readily be appreciated by one of ordinary skill in the art depending on the anatomical area with which the clip is to be used. For instance, within a heart, curved tissue engagement features may be sized, shaped, configured, and dimensioned so that the chordae tendineae do not catch on the curved tissue engagement features. Such configuration may be particularly beneficial when moving the leaflet clip when in an open configuration. For instance, if it is desired to reposition a leaflet clip (e.g., if a portion of the leaflet clip delivery and deployment system becomes caught on one or more chordae tendineae and bailout of the leaflet clip delivery and deployment system is an indicated course), the tissue engagement features will not engage or catch the chordae tendineae.

It will be appreciated that any of the engagement tissue features described herein may be provided on one or more arms of a leaflet clip which may or may not have an asymmetrical flex zone. Any number of tissue engagement features may be provided on one or more arms of a leaflet clip. Generally, at least one tissue engagement feature may be provided on each arm of a leaflet clip with at least two arms. In some embodiments, two or more tissue engagement features are provided on each leaflet clip arm. In some embodiments, the same number of tissue engagement features are provided on each leaflet clip arm. In other embodiments, a different number of tissue engagement features is provided on the leaflet clip arms (e.g., an even number of tissue engagement features on one leaflet clip arm and an odd number of tissue engagement features on another leaflet clip arm, or different numbers of an even number of tissue engagement features on the leaflet clip arms, or different numbers of an odd number of tissue engagement features on the leaflet clip arms). Spacing between adjacent tissue engagement features may be substantially constant, or may vary among the various tissue engagement features. The tissue engagement features on a leaflet clip arm, or among leaflet clip arms of a leaflet clip, need not all be of the size, shape, configuration, and/or dimension, and may be one or more of a variety of different shapes, thicknesses, projection heights, etc. Moreover, a leaflet clip delivery and deployment system may deliver and deploy, and/or include, one or more leaflet clips of different configurations. It will be appreciated that reference herein to a leaflet clip arm generally includes one or both or more (if the leaflet clip has more than two arms) of the arms of the leaflet clip.

Various embodiments of a leaflet clip delivery and deployment system and various embodiments of leaflet clips will now be described with reference to examples illustrated in the accompanying drawings. For the sake of brevity and convenience, and without intent to limit, common or similar elements of leaflets clips disclosed herein with common or similar functions are indicated with the same reference characters differing in value by 1000, reference being made to the above descriptions of similar elements and operations. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present disclosure is not limited to only the embodiments specifically described herein.

Turning now to the drawings, it will be appreciated that common features are identified by common reference elements and, for the sake of brevity and convenience, and without intent to limit, the descriptions of the common features are generally not repeated. For purposes of clarity, not all components having the same reference number are numbered. Moreover, a group of similar elements may be indicated by a number and letter, and reference may be made generally to one or more such elements as a group by the number alone (without including the letters associated with each similar element). It will be appreciated that, in the following description, elements or components similar among the various illustrated embodiments with reference numbers greater than 1000 are generally designated with the same reference numbers increased by a multiple of 1000 and redundant description is generally omitted for the sake of brevity. Moreover, certain features in one embodiment may be used across different embodiments and are not necessarily individually labeled when appearing in different embodiments.

An example of an embodiment of a leaflet clip delivery and deployment system 100 formed in accordance with various principles of the present disclosure is illustrated in FIG. 1 delivering a leaflet clip 1000 to a deployment or treatment site within a heart, and in position to deploy the leaflet clip 1000 on a heart valve leaflet L. It will be appreciated that terms such as deployment site, treatment site, etc. may be used interchangeably herein without intent to limit. The leaflet clip delivery and deployment system 100 may be delivered to the deployment site by a delivery catheter 102 which may be guided within a delivery guide sheath 104. The delivery catheter 102 and the delivery guide sheath 104 may be flexible tubular elements (e.g., catheter, sheath, shaft, tube, etc.) steerable through tortuous pathways through the body to allow for transluminal (in contrast with open surgery) delivery of a leaflet clip 1000. The leaflet clip 1000 may be any known leaflet clip, or a leaflet clip such as disclosed and described herein. Generally, the leaflet clip delivery and deployment system 100 delivers a leaflet clip 1000 having at least one ventricular clip arm 1012 configured to be positioned on a side of the heart valve leaflet L facing the heart ventricle, and at least one atrial clip arm 1014 configured to be positioned on a side of the heart valve leaflet L facing the heart atrium. In various examples of embodiments of leaflet clips 1000 disclosed herein, when the ventricular clip arm 1012 and the atrial clip arm 1014 of the leaflet clip 1000 are spaced apart from each other, tissue such as a heart valve leaflet L may be positioned therebetween. When the ventricular clip arm 1012 and the atrial clip arm 1014 are returned to a neutral configuration closer to each other, the heart valve leaflet L may be clamped between the ventricular clip arm 1012 and the atrial clip arm 1014, as described in further detail below. For the sake of convenience, the present disclosure references a leaflet clip 1000 with a ventricular clip arm 1012 and an atrial clip arm 1014 generally biased towards each other in a closed clamping configuration, and movable about a flex zone 1016 into an open configuration to accept body tissue such as a heart valve leaflet L between the arms 1012, 1014. However, it will be appreciated that the disclosed leaflet clip delivery and deployment system 100 and associated leaflet clip 1000 need not be so limited.

As illustrated in FIG. 1, a leaflet clip 1000 may be coupled to a clip spreader 110 for delivery with the clip spreader 110 to a deployment site. It will be appreciated that terms such as coupled with, engaged with, operatively associated with, carried by, etc. (and other grammatical forms thereof) may be used interchangeably herein without intent to limit. The clip spreader 110 may be provided at a distal end 101 of the leaflet clip delivery and deployment system 100, such as illustrated in FIG. 1. The illustrated leaflet clip 1000 has a ventricular clip arm 1012 and an atrial clip arm 1014 which may be manipulated by the clip spreader 110 to engage a heart valve leaflet L. In the illustrated example of an embodiment, the clip spreader 110 is configured to move at least one arm of the leaflet clip 1000 with respect to another arm of the leaflet clip 1000 to shift the leaflet clip 1000 into an open configuration to engage a heart valve leaflet L. In the example of an embodiment illustrated in FIG. 1, the clip spreader 110 is configured to move the ventricular clip arm 1012 away from the atrial clip arm 1014. The leaflet clip delivery and deployment system 100 thus may be extended through a heart valve HV so that the distal end 101 thereof, with the leaflet clip 1000, is within the ventricle V. Opening of the leaflet clip 1000, such as by actuating the clip spreader 110 to move the ventricular clip arm 1012 away from the atrial clip arm 1014, allows the heart valve leaflet L to enter the space within the leaflet clip 1000 between the arms 1012, 1014. Optionally, the leaflet clip delivery and deployment system 100 may be moved proximally towards the heart valve leaflet L to capture the heart valve leaflet L between the arms 1012, 1014. The ventricular clip arm 1012 may then be allowed to return to a neutral position closer to the atrial clip arm 1014, grasping the heart valve leaflet L therebetween. It will be appreciated that the term manipulated (and other grammatical forms thereof) may be used interchangeably herein with terms such as actuated, moved, controlled, maneuvered, etc., without intent to limit.

An example of an embodiment of a clip spreader 110 is illustrated in further detail in FIGS. 2-5. The clip spreader 110 includes a ventricular spreader arm 112 and an atrial spreader arm 114, which may be pivotably coupled together, such as about a hinge or pivot 116. The pivot 116 may be a pivot point or pin, or other structure allowing relative movement of the ventricular spreader arm 112 and the atrial spreader arm 114 such as known to those of ordinary skill in the art, the details of which are not critical to the present disclosure. The ventricular spreader arm 112 is configured to engage the ventricular clip arm 1012 of a leaflet clip 1000, and the atrial spreader arm 114 is configured to engage the atrial clip arm 1014 of the leaflet clip 1000. In embodiments in which the ventricular clip arm 1012 and the atrial clip arm 1014 of the leaflet clip 1000 are biased towards each other, coupling of the clip spreader 110 with the leaflet clip 1000 may allow the leaflet clip 1000 to maintain the ventricular spreader arm 112 and the atrial spreader arm 114 of the clip spreader 110 in a generally closed configuration until actuated into an open configuration (as described in further detail below).

In the example of an embodiment of a clip spreader 110 illustrated in FIGS. 1-6, the atrial spreader arm 114 is mounted on the delivery catheter 102 (e.g., to remain substantially stationary with respect to the delivery catheter 102), and the ventricular spreader arm 112 is movable with respect to the atrial spreader arm 114, although other configurations are within the scope and spirit of the present disclosure. The ventricular spreader arm 112 is movable between a delivery/deployment configuration illustrated in FIG. 2, and an actuated configuration illustrated in FIG. 3.

More particularly, in the delivery/deployment configuration, the ventricular spreader arm 112 is closer to the atrial spreader arm 114 than in the actuated configuration. The delivery/deployment configuration may be alternately referenced herein as a neutral, rest, unbiased, closed, compact, etc., (such terms being used interchangeably herein without intent to limit) configuration in which the ventricular spreader arm 112 is generally aligned (e.g., parallel) with the atrial spreader arm 114 to result in a generally streamlined or compact delivery configuration of the clip spreader 110 to facilitate deployment, such as within and/or through the delivery catheter 102. Additionally, in the delivery/deployment configuration, the leaflet clip 1000 is generally also in a delivery/deployment configuration with the ventricular clip arm 1012 in a compact configuration for delivery and in a position with respect to the atrial clip arm 1014 for deployment engaging tissue between the ventricular clip arm 1012 and atrial clip arm 1014. In the actuated configuration of the clip spreader 110, the ventricular spreader arm 112 is further from the atrial spreader arm 114 (than in the delivery/ deployment configuration) to allow tissue to be positioned therebetween and between the ventricular clip arm 1012 and the atrial clip arm 1014 of the leaflet clip 1000. In such configuration, the leaflet clip 1000 generally is considered to be in an actuated configuration as well, such configuration alternately referenced herein as biased, flexed, open, etc., without intent to limit. As may be appreciated with reference to FIG. 3 and FIG. 4, the clip spreader 110, when actuated into an open configuration as illustrated in FIG. 3, may be configured to accommodate the flex zone 1016 of the leaflet clip 1000, as may be appreciated with reference to FIG. 4, to alleviate undue stresses or strains on the flex zone 1016. For instance, a flex region 117 may be defined in the clip spreader 110, such as in the area of the pivot 116, to accommodate movement of the flex zone 1016 of the leaflet clip 1000 as the ventricular clip arm 1012 is moved apart from the atrial clip arm 1014 of the leaflet clip 1000.

In accordance with various principles of the present disclosure, the clip spreader 110 and/or the leaflet clip 1000 may be configured to be engaged with each other so that the leaflet clip 1000 is coupled to the clip spreader 110 and does not disengage therefrom until the leaflet clip 1000 is deployed in the desired/medically indicated position/location. Various structures and configurations of the clip spreader 110 and leaflet clip 1000 may be used within the scope of the present disclosure to achieve such engagement or retention (such terms, and various conjugations thereof, being used interchangeably herein without intent to limit). In accordance with various principles of the present disclosure, the leaflet clip 1000 is slidably coupled with respect to the clip spreader 110 so that relative translation or sliding movement between the leaflet clip 1000 and the clip spreader 110, such as axial sliding movement (e.g., along the longitudinal axis LA of the clip spreader 110 and/or the delivery catheter 102 and/or the leaflet clip 1000 and/or the leaflet clip delivery and deployment system 100) results in disengagement of the leaflet clip 1000 from the clip spreader 110. An example of an embodiment of engagement elements and features and structures allowing for such axial relative movement between the leaflet clip 1000 and the clip spreader 110 may be appreciated with reference to FIG. 3 and the cross-sectional view of FIG. 4 along-lines IV-IV of FIG. 2. It will be appreciated that terms such as axial movement, translation, sliding movement, etc. may be used interchangeably herein to refer to general relative movement of elements without unlocking or pivoting or further movements.

In the example of an embodiment of a leaflet clip delivery and deployment system 100 illustrated in FIG. 3, the ventricular spreader arm 112 of the clip spreader 110 and the ventricular clip arm 1012 of the leaflet clip 1000 have mating ventricular retention elements, and the atrial spreader arm 114 of the clip spreader 110 and the atrial clip arm 1014 of the leaflet clip 1000 have mating atrial retention elements. To reduce stresses in the leaflet clip 1000, it may be desirable for the respective retention elements of the clip spreader 110 and the leaflet clip 1000 to engage each other closer to the free ends 1011, 1015 of the ventricular clip arm 1012 and atrial clip arm 1014 of the leaflet clip 1000 than to the flex zone 1016 of the leaflet clip 1000. It will be appreciated that other configurations (e.g., only the ventricular components or only the atrial components having retention elements, different locations of the retention elements along the spreader arms and leaflet clip arms, etc.) are within the scope of the present disclosure.

In one embodiment, such as illustrated in FIG. 3, the ventricular spreader arm 112 includes a ventricular spreader arm retention element 122 in the form of a projection, and the ventricular clip arm 1012 of the leaflet clip 1000 includes a mating ventricular leaflet clip arm retention element 1022 in the form of a detent or aperture. In some embodiments, the ventricular spreader arm retention element 122 is in the form of a hook which extends into an aperture defined in the ventricular clip arm 1012 of the leaflet clip 1000 as the ventricular leaflet clip arm retention element 1022. The respective ventricular retention elements 122, 1022 of the clip spreader 110 and the leaflet clip 1000 accordingly may engage and disengage each other by relative sliding movement. Advantageously, the free end 121 of the ventricular spreader arm retention element 122 is directed towards the free end 111 of the ventricular spreader arm 112, and, when engaged with the ventricular leaflet clip arm retention element 1022, is directed to the free end 1011 of the ventricular clip arm 1012 of the leaflet clip 1000. As such, as may be appreciated with reference to FIG. 1, the ventricular clip arm 1012 of the leaflet clip 1000 is releasable from the clip spreader 110 when moved proximally with respect to the clip spreader 110, and generally along the longitudinal axis LA of the leaflet clip delivery and deployment system 100. As such, if the leaflet clip 1000 is clamped onto a heart valve leaflet L in an open position of the heart valve leaflet L, the heart valve leaflet L, as it closes to a coapted position, may carry the leaflet clip 1000 away from and off of the clip spreader 110 so that the leaflet clip 1000 remains deployed on the heart valve leaflet L, as described in further detail below.

In one embodiment, such as illustrated in FIG. 3 and FIG. 4, the atrial spreader arm 114 includes an atrial spreader arm retention element 124 in the form of a projection, and the atrial clip arm 1014 of the leaflet clip 1000 includes a mating atrial leaflet clip arm retention element 1024 in the form of a detent or aperture. In some embodiments, the atrial spreader arm retention element 124 is in the form of a boss insertable into an aperture defined in the atrial leaflet clip arm retention element 1024. A movable retention element 118 may be shiftable between an engaged position (as illustrated in FIG. 3 and FIG. 4) and a disengaged position. In the engaged position of the movable retention element 118, the movable retention element 118 engages the atrial spreader arm retention element 124 to maintain the atrial spreader arm retention element 124 engaged with the atrial leaflet clip arm retention element 1024. For instance, the movable retention element 118 may be a wire insertable through an aperture through the atrial spreader arm retention element 124 to prevent or inhibit movement of the atrial spreader arm retention element 124 with respect to the atrial leaflet clip arm retention element 1024 and thus to prevent or inhibit movement of the atrial clip arm 1014 of the leaflet clip 1000 with respect to the clip spreader 110. In the disengaged position of the movable retention element 118, the movable retention element 118 is positioned to allow relative movement of the leaflet clip 1000 and the clip spreader 110. For instance, a movable retention element 118 in the form of a wire, a filament, a tether, a cable (such as a Bowden cable), or the like may be moved proximally to withdraw from an atrial spreader arm retention element 124 in the form of a boss, thereby unblocking the leaflet clip 1000 from movement with respect to the clip spreader 110. The movement between the atrial spreader arm 114 and the atrial clip arm 1014 may be a generally sliding movement, and may not include further movements in other directions.

In accordance with various principles of the present disclosure, a leaflet clip delivery and deployment system may include an actuator operatively engaged with a clip spreader to actuate the clip spreader to shift between a delivery configuration and an open position facilitating deployment of a clip manipulated by the clip spreader. In some embodiments, an actuator is coupled to at least one of the arms of the clip spreader of a leaflet clip delivery and deployment system formed in accordance with various principles of the present disclosure. In an example of an embodiment of a leaflet clip delivery and deployment system 100 illustrated in FIG. 1, FIG. 2, and FIG. 5, an actuator 130 is provided to shift the arms 112, 114 of the clip spreader 110 relative to each other, such as by moving the ventricular spreader arm 112 with respect to the atrial spreader arm 114. In the illustrated example of an embodiment, the actuator 130 includes an actuator cable 132 having a distal end 131 coupled to the ventricular spreader arm 112 and a proximal end (not shown) accessible (e.g., outside the patient) by a medical professional to actuate the actuator 130. The actuator cable 132 may be a metal, polymer, or other suitable biocompatible material capable of withstanding the forces necessary to actuate the clip spreader 110 as well as able to be navigated through a tortuous pathway within the patient's body. In some embodiments, the actuator cable 132 is in the form of a Bowden cable extending from a proximal end of the leaflet clip delivery and deployment system 100 through a Bowden termination and pull cable passage 134, at which the outer cable housing 133 terminates. The inner cable 135 (e.g., pull wire) of the actuator cable 132 continues distally, around the distal end 101 of the leaflet clip delivery and deployment system 100 and around the flex zone 1016 of the leaflet clip 1000, to be coupled to a leaflet clip arm 112, 114 to be moved with respect to the other leaflet clip arm 114, 112, such as upon pulling the actuator cable 132 (e.g., both the outer cable housing 133 and the inner cable 135 proximally).

In some embodiments, the actuator 130 is coupled to the clip spreader 110 so that the distal end 131 thereof is positioned closer to the free end 111 of the ventricular spreader arm 112 than the remainder of the actuator 130, so that the actuator 130 extends distally away the point at which the actuator 130 is coupled to the ventricular spreader arm 112 and distally away from the free end 111 of the ventricular spreader arm 112 and toward the pivot 116. In other words, in some embodiments, the actuator 130 extends distally (initially, and not proximally) from its connection (at the distal end 131 of the actuator 130) with the clip spreader 110. As may be appreciated with reference to the cross-sectional view of FIG. 5, along line V-V of FIG. 2, the distal end 131 of the actuator cable 132 may be fixed to the ventricular spreader arm 112 such as via a cable holder 136 (e.g., a boss) mounted or coupled or otherwise fixed to the ventricular spreader arm 112. The distal end 131 of the actuator cable 132 may extend through a bore 137 within the cable holder 136 and have a widened distalmost end (e.g., the free end) to prevent the actuator cable 132 from being withdrawn from the bore 137 when actuating the ventricular spreader arm 112 to open. The widened distalmost end of the actuator cable 132 may be formed by the actuator cable 132 itself (e.g., a knot or loop, or a crimping or widening or flattening of the actuator cable 132), or by an element coupled thereto, such as a metal fitting 138 (e.g., crimped collar, cylinder, bead, overmolded holder positioned over the actuator cable 132, or a pin or other element about which the actuator cable 132 is wrapped, etc.). It will be appreciated that other manners of coupling an element, such as an actuator cable 132, of the actuator 130 to the clip spreader 110 (e.g., welding, brazing, adhering, interference fit, etc.) are within the scope and spirit of the present disclosure, the particulars of which are not critical to the general principles of the present disclosure.

The actuator cable 132 may extend from the distal end 131 thereof, around the clip spreader 110 (e.g., along the exterior of the clip spreader 110, with the leaflet clip 1000 positioned along the interior of the clip spreader 110), proximally along the ventricular spreader arm 112, and proximally to a proximal location at which the actuator cable 132 may be actuated (e.g., pulled) to move the ventricular spreader arm 112 to which the actuator cable 132 is coupled. In the example of an embodiment illustrated in FIG. 1, FIG. 2, and FIG. 5, the actuator cable 132 extends distally from the point at which the actuator cable 132 is coupled to the clip spreader 110, towards and around the distal end 101 of the leaflet clip delivery and deployment system 100, and then proximally along the clip spreader arm (e.g., along the exterior of the clip spreader 110) opposite the clip spreader arm to which the actuator cable 132 is coupled to a proximal location at which the actuator 130 may be controlled by a medical professional (e.g., via the proximal end of the actuator cable 132). It may be appreciated that such configuration generally allows for the optimal force vector to be applied to actuate the clip spreader 110. The actuator cable 132 may extend proximally within the delivery catheter 102 to a proximal end of the leaflet clip delivery and deployment system 100 at which the actuator cable 132 may be controlled.

In use, a leaflet clip delivery and deployment system 100 formed in accordance with various principles of the present disclosure may be delivered to a treatment site, such as a heart valve HV, as illustrated in FIG. 1. Although the mitral valve of a heart is illustrated in FIG. 1, principles of the present disclosure may be applied to the tricuspid valve, or other anatomical sites. The distal end 101 of the leaflet clip delivery and deployment system 100 is extended from the atrium into the ventricle, and the ventricular spreader arm 112 of the clip spreader 110 is actuated (such as with an actuator 130 as described above, or with another type or form of an actuator) to spread open the leaflet clip 1000, such as by moving the ventricular clip arm 1012 of the leaflet clip 1000 away from the atrial clip arm 1014 of the leaflet clip 1000. The heart valve leaflet L may either be allowed to enter between the ventricular clip arm 1012 and the atrial clip arm 1014 of the leaflet clip 1000, or the leaflet clip delivery and deployment system 100 is moved proximally (towards the heart valve leaflet L) so that a heart valve leaflet L is positioned between the ventricular clip arm 1012 and the atrial clip arm 1014 of the leaflet clip 1000. The ventricular clip arm 1012 is then allowed to return to a position closer to the atrial clip arm 1014 of the leaflet clip 1000, such as by allowing the ventricular spreader arm 112 to return to a position closer to the atrial spreader arm 114. For instance, an actuator 130 as described above may be actuated or released to release the ventricular spreader arm 112 from an open configuration. If for any reason it is desired or medically indicated to adjust the position of the leaflet clip 1000 (e.g., if a different position or orientation of the leaflet clip 1000 is desired and/or medically indicated, if any component of the leaflet clip delivery and deployment system 100 becomes caught on a chordae tendineae, etc.), the clip spreader 110 may be actuated again to release the leaflet clip 1000 and the leaflet clip delivery and deployment system 100 may be shifted to the desired position for deployment of the leaflet clip 1000. Once the leaflet clip 1000 is in the desired and/or medically indicated deployment position, the leaflet clip 1000 may be released from the clip spreader 110 in the deployed position. For instance, mating ventricular retention elements 122, 1022 and mating atrial retention elements 124, 1024 of the clip spreader 110 and the leaflet clip 1000, respectively, may be disengaged. In an embodiment as described above, a movable retention element 118 is shifted proximally to allow disengagement of the atrial leaflet clip arm retention element 1024 from the atrial spreader arm retention element 124. The ventricular leaflet clip arm retention element 1022 may then be slidingly disengaged from the ventricular spreader arm retention element 122. As noted above, movement of the heart valve leaflet L may move the leaflet clip 1000 away from the clip spreader 110 to release the ventricular leaflet clip arm retention element 1022 from the ventricular spreader arm retention element 122. Alternatively, the leaflet clip delivery and deployment system 100 may be moved proximally to disengage the ventricular spreader arm retention element 122 from the ventricular leaflet clip arm retention element 1022. Without being coupled to a leaflet clip 1000, the ventricular spreader arm 112 may remain in an open, configuration if desired, as illustrated in FIG. 5.

With the leaflet clip 1000 deployed, an artificial chordae tendineae 140 (coupled to the leaflet clip 1000 in any manner known to those of ordinary skill in the art) may be extended from the leaflet clip 1000 to the ventricle wall, as illustrated in FIG. 6. The artificial chordae tendineae 140 may be anchored to the ventricle wall (e.g., into papillary muscle) with an artificial chordae tendineae anchor 150 such as known to those of ordinary skill in the art, or such as described in the above-referenced patent applications incorporated herein or in patent application 63/239,469, titled "Devices, Systems, And Methods For Anchoring An Artificial Chordae Tendineae To Cardiac Tissue," and filed on even date herewith and incorporated by reference herein in its entirety for all purposes. It will be appreciated that the artificial chordae tendineae 140 may be coupled to the leaflet clip 1000 during delivery and deployment of the leaflet clip 1000 and extend out a side of the clip spreader 110 and laterally through a slot 141 in the leaflet clip delivery and deployment system 100 into an artificial chordae tendineae anchor 150 carried therein (e.g., as in FIG. 1).

In order to treat a heart valve HV, such as by treating a heart valve leaflet L, as illustrated in FIG. 1 and FIG. 6, tension on the artificial chordae tendineae 140 may be adjusted and then fixed/locked, such as with respect to the artificial chordae tendineae anchor 150. For instance, one or more leaflet clips 1000 formed in accordance with various principles of the present disclosure may be used to adjust the function of one or more leaflets L of a prolapsed valve with the use of an artificial chordae tendineae 140 tensioned to result in proper closure of the one or more leaflets L. For example, in the embodiments illustrated in FIG. 1 and FIG. 6, a mitral valve is treated with at least one leaflet clip 1000 formed in accordance with various principles of the present disclosure, and an artificial chordae tendineae 140 coupled to the leaflet clip 1000 and anchored to the heart ventricle V (e.g., to papillary muscle tissue thereof). Tension on the artificial chordae tendineae 1000 is adjusted until proper functioning of the heart valve leaflet L coupled thereto (e.g., proper coaptation of the heart valve leaflet L) is achieved. In order to determine if proper functioning of the heart valve leaflet L has been achieved, various techniques may be used. For instance, reduction (and, ideally, elimination) of mitral valve regurgitation may be assessed, such as by various imaging techniques (e.g., fluoroscopy, etc.) known or heretofore known to those of ordinary skill in the art (the details of which do not form a part of or limit the present disclosure, and thus are not provided herein). Tension on the artificial chordae tendineae 1000 may be adjusted until the desired effect on the heart valve leaflet L has been achieved.

As may be appreciated, it may be desirable to minimize any effect any of the various devices or components of a leaflet clip and/or leaflet clip delivery and deployment system and/or other devices or components associated therewith may have on the closure of a heart valve HV being treated, such as during the procedure. In accordance with various principles of the present disclosure, once a leaflet clip is deployed with respect to a heart valve leaflet L, associated devices or components may be moved away from the deployed leaflet clip to allow closure of the valve with minimal effect of devices or components remaining at the treatment site to complete the treatment of the leaflet (e.g., to adjust tension on the leaflet). For instance, as illustrated schematically in the plan view of a heart valve HV in FIG. 7, a leaflet clip (such as, though not limited to, a leaflet clip 1000 formed in accordance with various principles of the present disclosure) typically is deployed along the P2 segment of a posterior leaflet PL to treat the heart valve HV and/or the leaflets thereof. Once the leaflet clip 1000 has been deployed, further devices or components associated with the leaflet clip 1000 (such as an artificial chordae tendineae 140 and/or deployment devices associated therewith, and/or deployment devices associated with an artificial chordae tendineae anchor 150), illustrated schematically in broken lines in FIG. 7 and indicated generally with reference number 100', may be moved away from the site of deployment of the leaflet clip 1000. For instance, the devices/components 100' may be moved to be generally seated with respect to (at, in, along, etc.) a cleft of the posterior leaflet PL (e.g., cleft CL1, between the P2 segment and the P1 segment of the posterior leaflet PL, or cleft CL3, between the P2 segment and the P3 segment of the posterior leaflet PL) and/or a commissure of the heart valve HV (e.g., posteromedial commissure PMC or anterolateral commissure ALC). Various positions of devices/components 100' are shown schematically in FIG. 7 for the purpose of illustration and not limitation. It has been discovered that once the devices/components 100' are positioned with respect to a cleft or commissure in accordance with various principles of the present disclosure, the functioning of the heart valve HV may be observed to complete treatment thereof with minimal interference of the devices/components 100'.

It will be appreciated that a device such as a leaflet clip may be deployed additionally or alternatively with respect to any of the segments P1, P2, P3 of the posterior leaflet PL and/or any of the segments A1, A2, A3 of the anterior leaflet AL and/or to any of the leaflets of a tricuspid valve, or any other anatomical structures which may benefit from various aspects of the present disclosure. Additionally or alternatively, it will be appreciated that the above-described technique of deploying a treatment device (such as a leaflet clip) with respect to a heart valve leaflet to treat a heart valve (or other anatomical structure), and thereafter repositioning devices or components associated with the deployed device (e.g., to a heart valve cleft or commissure) may be used with devices, systems, components, etc., other than those disclosed herein.

As noted above, a variety of leaflet clips formed in accordance with various principles of the present disclosure may be used with a leaflet clip delivery and deployment system 100. Various example of embodiments of leaflet clips are described with reference to FIGS. 8-15. It will be appreciated that each disclosed embodiment may include one or more features or structures which may be separately and independently usable in another embodiment even if not illustrated in such other embodiment.

A leaflet clip may be formed in accordance with various principles of the present disclosure from an elongated elastic and/or shape memory material, such as Nitinol, formed (e.g., by heat treating) into the desired configuration. In some embodiments, the leaflet clip is formed as a monolithic one-piece element. In some embodiments, the leaflet clip is formed from an initially substantially straight element (e.g., a rod or strip) which is formed or bent into the desired shape with leaflet clip arms positioned together to grasp tissue therebetween. The forming process may include a series of bending steps, optionally including heat treatment, to bend the substantially straight element into the desired bent configuration of a leaflet clip. The material may be bent about a mandrel to form the flex zone (e.g., as a bent region between the leaflet clip arms which grasp tissue therebetween). The leaflet clip may be formed from a heat set material so that the final shape is retained. Additionally or alternatively, the leaflet clip may be formed from a shape memory material so that if the leaflet clip is straightened, potential energy is generated to restore the leaflet clip to its formed bent configuration to grasp tissue between the leaflet clip arms. The material may be electropolished to remove approximately 0.0075 in (0.1905 mm) of material, optionally from all sides/surfaces of the clip, such as to remove any high stress concentration from processing. In some embodiments, to facilitate wider opening of the leaflet clip (spreading the leaflet clip arms further apart) without overstraining the leaflet clip (such as at the flex zone), the thickness of the leaflet clip (from an inner or interior side along which the leaflet clip arms face each other, to an outer or exterior side such as along which the actuator 130 extends) increases from a free end of a leaflet clip arm to the flex zone. In one configuration, the thickness may increase from a thickness of approximately 13.6 mil (0.345 mm) along at least a portion of a free end of one leaflet clip arm (e.g., the ventricular arm), to a thickness of approximately 15 mil (0.381 mm) along the flex zone, and then decrease to a thickness of approximately 14.3 mil (0.363 mm) along the other leaflet clip arm (e.g., the atrial leaflet clip arm). In another configuration, the thickness may increase from a thickness of approximately 10 mil (0.254 mm) along at least a portion of a free end of one leaflet clip arm (e.g., the ventricular arm), to a thickness of approximately 13.5 mil (0.343 mm) along the flex zone, and then decrease to a thickness of approximately 11.6 mil (0.295 mm). The increase in thickness along the flex zone may inhibit or prevent strain from concentrating at the flex zone (e.g., at the middle of the flex zone), and may allow the leaflet clip to open further (allow the leaflet clip arms to be extended apart from each other further) than if the leaflet clip had a uniform thickness.

With reference to FIG. 8, an example of an embodiment of a leaflet clip 2000 formed in accordance with various principles of the present disclosure is illustrated. The illustrated leaflet clip 2000 includes two arms 2012, 2014 coupled along a flex zone 2016 which may be configured to bias the arms 2012, 2014 into a closed configuration oriented toward each other. Each arm 2012, 2014 includes protrusions 2018, such as teeth in the embodiment illustrated in FIG. 8, configured to embed into tissue. The protrusions 2018 may have smooth surfaces extending (e.g., at an angle) from the free ends 2011, 2015 of the arms 2012, 2014 towards the flex zone 2016 and configured to accept a tissue moving between the arms 2012 2014. Each protrusion 2018 may include an engaging end 2019 (e.g., at a free end thereof) configured to embed into or grasp or otherwise engage a tissue between the arms 2012 2014, and optionally also to resist withdrawal of the engaged tissue. In accordance with various principles of the present disclosure, the leaflet clip arm 2012 may be configured to be positioned along a ventricular side of a heart valve leaflet L (and thus referenced herein as a ventricular clip arm 2012) and the leaflet clip arm 2014 may be configured to be positioned along an atrial side of a heart valve leaflet L (and thus referenced herein as an atrial clip arm 2014). Moreover, in accordance with various principles of the present disclosure, the flex zone 2016 may be asymmetrical to accommodate closure of a heart valve leaflet L. More particularly, the atrial clip arm 2014 of the example of an embodiment of a leaflet clip 2000 is substantially straight, whereas the ventricular clip arm 2012 of the leaflet clip 2000 may extend outwardly (in a direction away from the atrial clip arm 2014) towards an outwardly expanded flex zone 2016. Such expanded flex zone 2016 along the ventricular clip arm 2012 distributes stress and strain more evenly than if not expanded (e.g., such as along the atrial clip arm 2014), whereas the unexpanded region of the flex zone 2016 along the atrial clip arm 2014 allows better coaptation of a heart valve leaflet L to which the leaflet clip 2000 is clamped than may be achieved with an expanded flex zone region along the atrial side of the leaflet clip 1000. It will be appreciated that the free ends of ventricular clip arm 2012 and atrial clip arm 2014 are configured as in U.S. Patent Application Publication US2021/0007847 (incorporated hereinabove by reference), but may instead be configured similar to the ventricular clip arm and atrial clip arm of other leaflet clips disclosed herein.

In accordance with various principles of the present disclosure, instead of both arms of a leaflet clip having protrusions, another example of an embodiment of a leaflet clip 3000, as illustrated in FIG. 9, may have protrusions 3018 along only one of the arms 3012, 3014. The illustrated protrusions 3018 are shown on an atrial clip arm 3014 of the leaflet clip 3000, such as to facilitate initial engagement and grasping of tissue. However, the protrusions 3018 may be provided, instead, only on the ventricular clip arm 3012.

Alternatively, as in the examples of embodiments of leaflet clips 4000, 5000, 6000 illustrated in FIG. 10, FIG. 11, and FIG. 12, the sharper protrusions may be formed on one arm and smoother protrusions may be formed on the other arm. The "smoother" protrusions may be duller, or less jagged, or more rounded or curved, or otherwise not as sharp as the teeth on the opposite arm. Fillets may be included on the outer edges (e.g., corners or edges may be rounded), such as to prevent impacting adjacent structures (such as an artificial chordae tendineae 140 or native chordae tendineae or other tissue). The "sharper" protrusions may be more angled or angular than the "smoother" protrusions. Additionally or alternatively, the "sharper" protrusions may have a height distance away from the leaflet arm greater than a width along the leaflet arm whereas the "smoother" protrusions may have a height distance away from the leaflet arm less than a width along the leaflet arm. For instance, the sharper protrusions 4018a, 5018a, 6018a of the leaflet clips 4000, 5000, 6000 may be provided on one arm in the form of teeth (such as in the example of an embodiment illustrated in FIG. 8), and the duller protrusions 4018b, 5018b, 6018b may be provided on the other arm in the form of curved protrusions such as bumps or ripples or curves or the like. In the illustrated embodiments, the smoother protrusions are advantageously provided on the ventricular clip arm 4012, 5012, 6012, such as not to form a catchpoint for tissue such as chordae tendineae. The bumps on the ventricular clip arm 4012, 5012, 6012 may be configured and positioned to engage tissue extending between the teeth on the atrial clip arm 4014, 5014, 6014, respectively, such as to enhance grasping of tissue between the opposite arms of the respective leaflet clips 4000, 5000, 6000. As may be appreciated upon comparing the configurations of the smoother protrusions illustrated in FIGS. 10-12, the thickness/height (in a direction away from the leaflet arm) and/or the width/length (in a direction along the leaflet arm) may be varied, such as to optimize interaction with the sharper protrusions. Moreover, the smoother protrusions may be formed by a thickening of the clip arm (e.g., as in the examples of embodiments illustrated in FIG. 10 and FIG. 11), or by creating a ripple or wave or a series of bends/curves in the clip arm (as in the example of an embodiment illustrated in FIG. 12).

It will be appreciated that the sharper protrusions 2018, 3018, 4018a, 5018a, 6018a may be formed as projections (e.g., machined or molded or otherwise formed from the material of the respective leaflet clips 2000, 3000, 4000, 5000, 6000), as illustrated in FIG. 8, FIG. 9, FIG. 10, FIG. 11, and FIG. 12, respectively. Additionally or alternatively, sharper protrusions 7018 may be formed by forming slits in one or both of the arms 7012, 7014 of a leaflet clip 7000, as illustrated in FIG. 13, and bent or otherwise deformed into projections. It will be appreciated that the flex zone 7016 of leaflet clip 7000 may be asymmetric, such as the asymmetric flex zone 2016 of the example of an embodiment of a leaflet clips 2000 illustrated in FIG. 8.

It will be appreciated that the number, spacing between, relative placement, distribution, sizes, shapes, dimensions, and configurations of the protrusions 2018, 3018, 4018a, 4018b, 5018a, 5018b, 6018a, 6018b, 7018 of the various examples of embodiments illustrated in FIG. 8, FIG. 9, FIG. 10, FIG. 11, FIG. 12, and FIG. 13, respectively, may be varied without departing from the spirit and scope of the present disclosure. For instance, different numbers of protrusions may be provided on the opposing arms of a given leaflet clip, the spacing between protrusions may vary, the angles of the protrusions may not be the same on a given leaflet clip arms, etc. In various embodiments, a leaflet clip formed in accordance with various principles of the present disclosure may be manufactured to be made up of a material adequate to provide a sufficient clamping force to fixate the clip to a heart valve leaflet, and to provide a substantial anchoring body for an attached filament such as an artificial chordae tendineae. In accordance with various principles of the present disclosure, the flex zone of any of the various leaflet clips 1000, 2000, 3000, 4000, 5000, 6000, 7000 may be formed (sized, shaped, configured, dimensioned, etc.) to allow a spring force sufficient to permit flexing open of the clip arms for entry of tissue therebetween, yet also to permit the clip arms to clamp onto the tissue with sufficient force so as not to readily be pulled off (not to be pulled off under normal use conditions readily appreciated by those of ordinary skill in the art). The thickness of the leaflet clips 1000, 2000, 3000, 4000, 5000, 6000, 7000 at their respective clamp zones 1016, 2016, 3016, 4016, 5016, 6016, 7016 is selected to allow the desired flexing and clamping force without resulting in plastic deformation of the clip. In some embodiments, the flex zone is sized, shaped, configured, and dimensioned to allow opening of the clip arms of at least up to approximately 90° (apart from each other), and, more preferably, at least up to approximately 135°, and even up to approximately 180° (including increments of 1° between 90° and) 180°. An example of an embodiment of a leaflet clip 1000 is illustrated in FIG. 14 with the flex zone 1016 allowing opening of the leaflet clip arms 1012, 1014 to be approximately 135° apart. An example of an embodiment of a leaflet clip 1000 is illustrated in FIG. 15 with the flex zone 1016 allowing opening of the leaflet clip arms 1012, 1014 to be approximately 180° apart.

In an aspect, a clip may be manufactured to provide sufficient force to enable the clip to fixedly attach to tissue without imparting undue gravitational forces that may disrupt surgical repair efforts. In this way, the clip has a mass that is not significantly larger than necessary such that the weight of the clip does not negatively impact the leaflet or nearby tissue. For example, a clip may weigh less than about 0.10 grams, less than about 0.08 grams, or the like, e.g. such that a weight of a clip may not undesirably interfere with leaflet operation. A clip may comprise various materials such as, e.g., nitinol, a polymer, a rubber, nylon, stainless steel, nickel titanium, platinum, combinations thereof, or the like.

Although embodiments of the present disclosure may be described with specific reference to mitral valves, devices, systems, and methods such as disclosed herein may be used in connection with repair or modification of any valve annulus, for example including a tricuspid valve annulus, and/or any other dilatation, valve incompetency, valve leakage, and other similar heart failure conditions, and/or any other procedure which involve clamping tissue which may be subjected to forces such as palpatory forces or otherwise. Although embodiments of the present disclosure may be described with specific reference to medical devices and systems (e.g., transluminal devices inserted through a femoral vein or the like) for selective access to heart tissue, it should be appreciated that such medical devices and systems may be used in a variety of medical procedures, including, but not limited to, other procedures that require clamping a leaflet of a valve or clamping a tissue wall. Moreover, although disclosure herein of a clip delivery and deployment system and associated components and methods of use thereof are made with reference to a heart valve leaflet, other applications and uses are within the scope of the present disclosure. The disclosed medical devices and systems may also be inserted via different access points and approaches, e.g., percutaneously, endoscopically, laparoscopically, or combinations thereof.

In view of the above, it should be understood that the various embodiments illustrated in the figures have several separate and independent features, which each, at least alone, has unique benefits which are desirable for, yet not critical to, the presently disclosed leaflet clip delivery and deployment device, system, and method. Therefore, the various separate features and structures described herein need not all be present in order to achieve at least some of the desired characteristics and/or benefits described herein. Only one of the various features or structures may be present to achieve a desired characteristic and/or benefit described herein. Alternatively, one or more of the features or structures described with reference to one embodiment can be combined with one or more of the features or structures of any of the other embodiments provided herein. That is, any of the features described herein can be mixed and matched to create hybrid designs, and such hybrid designs are within the scope of the present disclosure. Moreover, throughout the present disclosure, reference numbers are used to indicate a generic element or feature of the disclosed embodiment. The same or similar reference number may be used to indicate elements or features that are not identical in form, shape, structure, etc., yet which provide similar functions or benefits. Additional reference characters (such as letters, as opposed to numbers) may be used to differentiate similar elements or features from one another.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied.

Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" and/or "includes/including" does not exclude the presence of other elements, components, features, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A leaflet clip delivery and deployment system comprising:

a clip spreader having an atrial spreader arm and a ventricular spreader arm; and a leaflet clip having an atrial clip arm and a ventricular clip arm;

wherein:

the atrial spreader arm and the atrial clip arm having mating atrial retention elements configured to retain the atrial spreader arm and the atrial clip arm together;

the ventricular spreader arm and the ventricular clip arm having mating ventricular retention elements configured to retain the ventricular spreader arm and the ventricular clip arm together; and at least one of the mating atrial retention elements or the mating ventricular retention elements are configured for sliding engagement and disengagement;

wherein the clip spreader comprises a recess configured to accommodate a flex zone of the leaflet clip about which the atrial clip arm and the ventricular clip arm move between an open configuration for accepting tissue therebetween and a closed configuration for clamping onto tissue.

2. The leaflet clip delivery and deployment system of claim 1, wherein at least one of the atrial retention element of the atrial clip arm or the ventricular retention element of the ventricular clip arm comprises an aperture.

3. The leaflet clip delivery and deployment system of claim 2, wherein the ventricular retention element of the ventricular spreader arm comprises a hook configured to engage within a ventricular retention element of the ventricular clip arm in the form of an aperture, and to disengage from the aperture by a sliding movement.

4. The leaflet clip delivery and deployment system of claim 3, wherein the leaflet clip is disengaged from the clip spreader by relative distal sliding movement of the ventricular retention element of the ventricular spreader arm or proximal sliding movement of the ventricular retention element of the ventricular clip arm.

5. The leaflet clip delivery and deployment system of claim 3, wherein:

the atrial retention element of the atrial spreader arm comprises a boss configured to mate within an atrial retention element of the atrial clip arm in the form of an aperture; and the atrial retention element further comprises a movable retention element in the form of a wire shiftable between an engaged position engaged with the boss to maintain the atrial spreader arm and the atrial clip arm engaged, and a disengaged position disengaged from the boss and allowing the atrial spreader arm and the atrial clip arm to disengage from each other as a result of relative movement therebetween.

6. The leaflet clip delivery and deployment system of claim 2, wherein the atrial retention element of the atrial spreader arm comprises a boss configured to mate within an atrial retention element of the atrial clip arm in the form of an aperture.

7. The leaflet clip delivery and deployment system of claim 6, wherein the atrial retention element further comprises a movable retention element shiftable between an engaged position maintaining the atrial spreader arm and the atrial clip arm engaged, and a disengaged position allowing the atrial spreader arm and the atrial clip arm to disengage from each other as a result of relative movement therebetween.

8. The leaflet clip delivery and deployment system of claim 7, wherein the movable retention element is shiftable between an engaged position engaged with the boss and a disengaged position disengaged from the boss.

9. The leaflet clip delivery and deployment system of claim 1, wherein:

the clip spreader comprises a pivot between the atrial spreader arm and the ventricular spreader arm;

the leaflet clip comprises a flex zone between the atrial clip arm and the ventricular clip arm;

the flex zone biases the atrial clip arm and the ventricular clip arm into a closed configuration for clamping onto tissue and flexes to allow the atrial clip arm and the ventricular clip arm to move apart from each other;

the atrial clip arm and the ventricular clip arm and the flex zone hold the atrial spreader arm and the ventricular spreader arm in a closed configuration; and the leaflet clip delivery and deployment systems further comprise a clip spreader actuator having a distal end coupled to the ventricular spreader arm at a coupling point, the clip spreader actuator extending distally from the coupling point, around the clip spreader, proximally along the ventricular spreader arm, and proximally to a proximal end thereof.

10. A method of deploying a leaflet clip having an atrial clip arm and a ventricular clip arm coupled together by a flex zone, the method comprising:

slidably engaging at least one of the atrial clip arm or the ventricular clip arm with a corresponding atrial spreader arm or ventricular spreader arm of a clip spreader;

deploying the leaflet clip to clamp onto another element;

slidably moving the leaflet clip and the clip spreader relative to each other to cause the at least one of the atrial clip arm or the ventricular clip arm to release from the clip spreader;

clamping the leaflet clip onto a leaflet; and distally advancing the clip spreader with respect to the clamped leaflet to slidingly disengage the leaflet clip and the clip spreader.

11. The method of claim 10, further comprising:

clamping the leaflet clip onto a leaflet; and sliding the leaflet clip off the clip spreader.

12. The method of claim 11, further comprising extending an artificial chordae tendineae from the leaflet clip to a ventricle wall, moving components associated with the artificial chordae tendineae away from the deployment site of the leaflet clip and into a commissure or cleft of the leaflet, adjusting tension on the artificial chordae tendineae, and observing the functioning of the leaflet.

13. The method of claim 11, wherein the ventricular clip arm is slidably engaged with the ventricular spreader arm such that movement of a leaflet clamped between the atrial clip arm and the ventricular clip arm slides the ventricular clip arm out of engagement with the ventricular spreader arm.

14. A leaflet clip delivery and deployment system comprising:

a clip spreader having an atrial spreader arm and a ventricular spreader arm; and a leaflet clip having an atrial clip arm and a ventricular clip arm;

wherein:

the atrial spreader arm and the atrial clip arm having mating atrial retention elements configured to retain the atrial spreader arm and the atrial clip arm together;

the ventricular spreader arm and the ventricular clip arm having mating ventricular retention elements configured to retain the ventricular spreader arm and the ventricular clip arm together;

at least one of the mating atrial retention elements or the mating ventricular retention elements are configured for sliding engagement and disengagement;

wherein at least one of the atrial retention element of the atrial clip arm or the ventricular retention element of the ventricular clip arm comprises an aperture;

wherein the atrial retention element of the atrial spreader arm comprises a boss configured to mate within an atrial retention element of the atrial clip arm in the form of an aperture; and wherein the atrial retention element further comprises a movable retention element shiftable between an engaged position maintaining the atrial spreader arm and the atrial clip arm engaged, and a disengaged position allowing the atrial spreader arm and the atrial clip arm to disengage from each other as a result of relative movement therebetween.

\* \* \* \* \*